(12) United States Patent
Berger et al.

(10) Patent No.: US 8,293,886 B2
(45) Date of Patent: Oct. 23, 2012

(54) SENSIZITATION OF CANCER CELLS TO THERAPY USING SINA TARGETING GENES FROM THE 1P AND 19Q CHROMOSOMAL REGIONS

(75) Inventors: Francois Berger, Meylan (FR); Laurent Pelletier, Echirolles (FR); Jean-Paul Issartel, Saint Egreve (FR); Sandra Boccard, Crolles (FR)

(73) Assignee: Universite Joseph Fourier, Grenoble (FR)

( * ) Notice: Subject to any disclaimer, the term of this patent is extended or adjusted under 35 U.S.C. 154(b) by 0 days.

(21) Appl. No.: 13/053,394

(22) Filed: Mar. 22, 2011

(65) Prior Publication Data

US 2011/0294867 A1 Dec. 1, 2011

Related U.S. Application Data

(62) Division of application No. 12/375,960, filed as application No. PCT/IB2007/003269 on Jul. 23, 2007, now Pat. No. 7,939,653.

(30) Foreign Application Priority Data

Jul. 31, 2006 (EP) .................................... 06291241

(51) Int. Cl.
*C07H 21/04* (2006.01)
*A61K 31/70* (2006.01)

(52) U.S. Cl. ........................................ 536/24.5; 514/44

(58) Field of Classification Search .................. None
See application file for complete search history.

(56) References Cited

U.S. PATENT DOCUMENTS

| 2003/0143732 A1 | 7/2003 | Fosnaugh et al. |
| 2004/0265230 A1 | 12/2004 | Martinez et al. |
| 2006/0134189 A1 | 6/2006 | Maclachlan et al. |
| 2007/0031844 A1 | 2/2007 | Khvorova et al. |

FOREIGN PATENT DOCUMENTS

| WO | 03/070918 | 8/2003 |
| WO | 2005/123953 | 12/2005 |

OTHER PUBLICATIONS

Chang, I.Y. et al., "Small Interfering RNA-Induced Suppression of ERCC1 Enhances Sensitivity of Human Cancer Cells to Cisplatin", Biochemical and Biophysical Research Communications, Feb. 4, 2005, pp. 225-233, vol. 237, No. 1, Academic Press Inc., Orlando, FL XP004697918.

Selvakumaran, M. et al., "Enhanced Cisplatin Cytotoxicity by Disturbing the Nucleotide Excision Repair Pathway in Ovarian Cancer Cell Lines", Cancer Research, American Association for Cancer Research, Mar. 15, 2003, pp. 1311-1316, vol. 63, No. 6 XP002321157.

EP Search Report dated Jan. 7, 2007 from corresponding EP 06291241.

*Primary Examiner* — Tracy Vivlemore
(74) *Attorney, Agent, or Firm* — Young & Thompson

(57) ABSTRACT

The invention relates to the identification of genes involved in resistance of cancer cells to therapy, to short nucleic acid molecules which inhibit the expression of these genes by RNA interference and to their use as adjuvant in cancer therapy, to sensitize cancer cells to conventional anticancer agents; the short nucleic acid molecules are double-stranded short interfering nucleic acid molecules including a sense and an antisense region, wherein the sense region includes a nucleotide sequence that is selected from the group consisting of: the sequences SEQ ID NO: 15, 11, 13, 14, 30, 31, 38, 46, 64 and 70 and the sequences having at least 70% identity, preferably at least 80% identity, more preferably at least 90% identity with the sequences, and the antisense region includes a nucleotide sequence that is complementary to the sense region.

Figure 1:
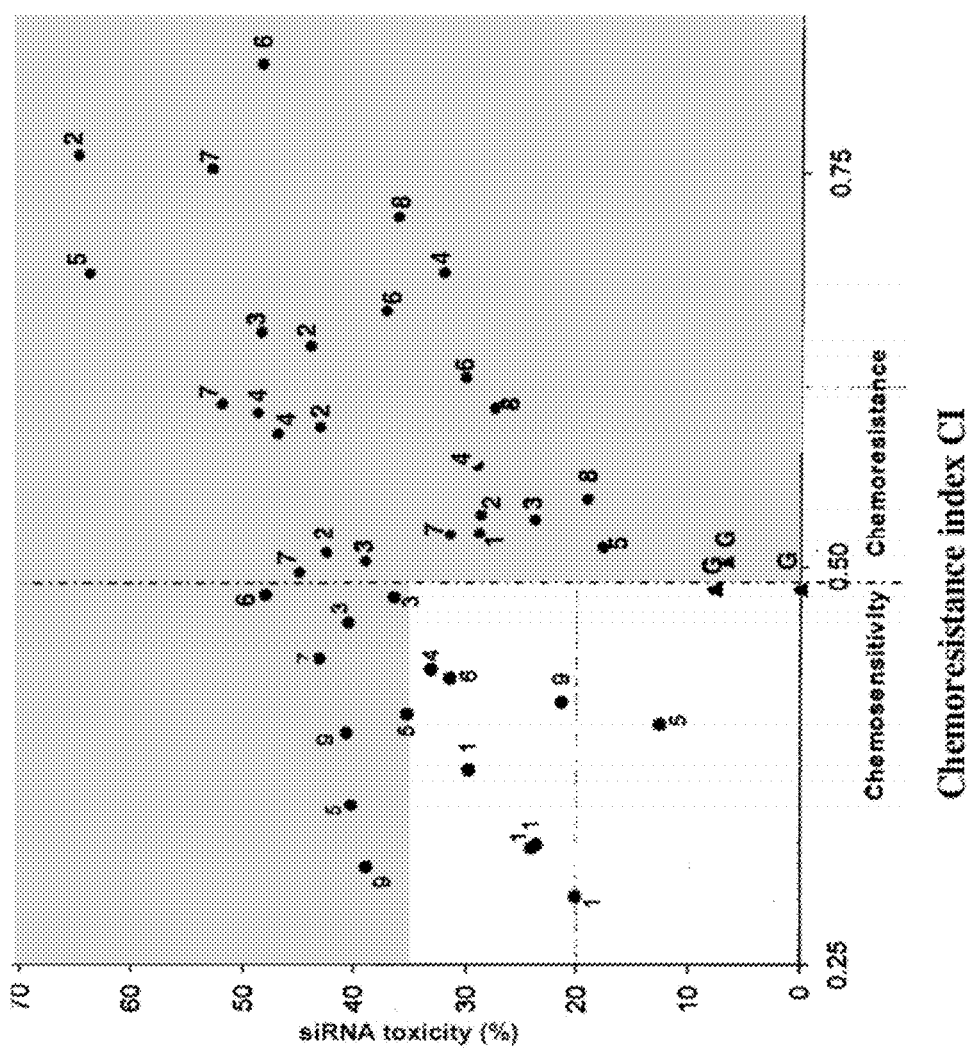

22 Claims, 3 Drawing Sheets ns
SENSIZITATION OF CANCER CELLS TO THERAPY USING SINA TARGETING GENES FROM THE 1P AND 19Q CHROMOSOMAL REGIONS

This application is a new divisional application of co-pending application Ser. No. 12/375,960 filed on Nov. 16, 2009, which is a 371 National stage application of PCT/IB07/03269 filed on Jul. 23, 2007, which claims priority to European Application No. 06291241.5 filed on Jul. 31, 2006. The entire contents of each of the above-identified applications are hereby incorporated by reference.

The invention relates to the identification of genes involved in resistance of cancer cells to therapy, to short nucleic acid molecules which inhibit the expression of these genes by RNA interference and to their use as adjuvant in cancer therapy, to sensitize cancer cells to conventional anticancer agents.

Gliomas are the most prevalent primary brain tumours. Among them, astrocytomas are a notable source of preoccupation in oncology because their incidence continually increases in industrialized countries (Ohgaki, H. and Kleihues, P., Acta Neuropathol., 2005, 109, 93-108) and, above all, their prognostic is pessimistic because they are refractory to even the most aggressive therapy. For example, median survival time in a patient with glioblastoma multiform (GBM), the worst grade of astrocytoma, is between 6 to 15 months after diagnosis (Chinot, O. et Martin, P. M., Biologie des tumeurs cérébrales gliales, 1996, Montpellier, France). Standard treatment is surgery followed by radiotherapy and chemotherapy. Recently, a large phase III study demonstrated that temozolomide (Temodal) therapy associated to radiotherapy provided a modest 3 months increase survival in glioblastoma (Stupp et al., N. Engl. J. Med., 2005, 352, 987-996).

Numerous works have addressed the chemoresistance as the principal cause of therapeutic fail (Harris, A. L., Int. J. Radiat. Biol. Relat. Stud. Phys. Chem. Med., 1985, 48, 675-680).

Contrasting with astrocytomas, oligodendrogliomas have a dramatic chemosensitivity (Perry et al., Arch. Neurol., 1999, 56, 434-436) resulting in a median survival of 10 years after medical management. Oligodendroglioma response to chemotherapy has been correlated with the loss of heterozygosity (LOH) on 1p and 19q chromosomal arms (Cairncross et al., J. Natl. Cancer Inst., 1998, 90, 1473-1479) with a common chromosomic area including 1p32-36 and 19q13.2-4 (Smith et al., Oncogene, 1999, 18, 4144-4152).

The major part of studies addressing the chemoresistance of astrocytomas concerned drug efflux mechanisms. However, the data are scattered and conflicting (Ashmore et al., Anticancer drugs, 1999, 10, 861-872). Expression of MDR-1 P-glycoprotein (P-gp), a protein associated with MDR, was not preferentially detected in resistant gliomas (Demeule et al., Int. J. Cancer, 2001, 93, 62-66). Moreover, MDR-type drug resistance in glioma cell lines results of long-term culturing, and in vivo, only cerebral endothelium induces this mechanism (Bahr et al., Brain Pathol., 2003, 13, 482-494). Finally, MDR-related genes were not located in the common 1p/19q deletion.

The correlation between 1p/19q LOH and oligodendrogliomas chemosensitivity strongly suggests that the reduction of global expression of some genes in the common region of deletion could be responsible for the observed chemosensitivity.

An adjuvant treatment targeting these genes could increase the chemosensitivity of cancer cells.

The completion of human genome sequencing provides the opportunity to investigate potential candidates among the 1,700 genes located in the 1p/19q LOH region.

Some studies have focused the search on genes with potential oncogenic properties, which inactivation would lead to oligodendroglioma oncogenesis but no convincing results were obtained to date.

Numerous genes located in the 1p/19q chromosomal regions (LOH regions) could have potential impact on drug resistance, including those involved in drug efflux systems, metabolism, apoptosis, cell-cycle regulation and DNA-repair.

To date, the correlation between gene expression and drug resistance has been demonstrated for two genes of the Nucleotide Excision Repair (NER) system, extensively studied in cancer cells: the ERCC1 and ERCC2 genes. Furthermore, a functional involvement of these genes in drug resistance has been established for the ERCC1 gene only.

Chemotherapy drugs commonly employed, such as PCV regimen (procarbazine, lomustine or CCNU, and vincristine), cisplatin, fotemustine, or temozolomide, are DNA-alkylating molecules. These drugs damage DNA leading cells to apoptosis. Cells can correct chemotherapy-induced alterations thanks to various DNA-repair mechanisms (Li et al., Anticancer Res., 2000, 20, 645-652; Wu et al., Clin. Cancer Res., 2003, 9, 5874-5879) and thus overcome treatment. This phenomenom is responsible for chemoresistance (Bosken et al., J. Natl. Cancer Inst., 2002, 94, 1091-1099).

A major role of ERCC1 in reparation of DNA alterations related to alkylating chemotherapy has been reported (Chaney S. G. & Sancar A., J. Natl. Cancer Inst., 1996, 88, 1346-1360; Li et al., Anticancer Res., 2000, 20, 645-652). Suppression of ERCC 1 expression in vitro by antisense or siRNA technology, leads to a decreased repair activity and an increased sensitivity of cultured cell lines to platinum-based anticancer agents (Selvakumaran et al., Cancer Res., 2003, 63, 1311-1316; Youn et al., Cancer Res., 2004, 64, 4849-4857; Chang et al., Biochem. Biophys. Res. Commun., 2005, 327, 225-233).

ERCC2 (XPD) expression has been correlated with resistance to alkylating compounds in numerous cell lines (Chen et al., Ai Zheng, 2002, 21, 233-239; Xu et al., Anticancer drugs, 2002, 13, 511-519), comprising glioma cell lines (Chen et al., Neurosurgery, 1998, 42, 1112-1119) and it has been reported that its overexpression increased DNA repair in glioma cell lines (Chen et al., Chin. Med. J., 2003, 116, 1171-1174). However, a functional involvement of ERCC2 in drug resistance has not been established.

RNAi interference is the process where the introduction of double-stranded RNA into a cell inhibits gene expression in a sequence dependent fashion (reviewed in Shuey et al., Drug Discovery Today, 2002, 7, 1040-1046). RNAi has been observed in a number of organisms such as mammalian, Drosophila, nematodes, fungi and plants and is believed to be involved in anti-viral defense, modulation of transposon-activity and regulation of gene expression. RNAi is usually described as a post-transcriptional gene-silencing mechanism in which dsRNA triggers degradation of homologous messenger RNA in the cytoplasm. Target recognition is highly sequence specific since one or two base pair mismatches between the siRNA and the target gene will greatly reduce silencing effect. The mediators of RNA interference are 21- and 23-nucleotide small interfering RNAs (siRNA). In a second step, siRNAs bind to a ribonuclease complex called RNA-induced silencing complex (RISC) that guides the small siRNA to its homologous mRNA target. Consequently, RISC cuts the mRNA approximately in the middle of the region paired with the antisense siRNA, after which the mRNA is further degraded. Therefore, the use of exogenous siRNA holds great promise as a new tool for mammalian functional genomics and may also have future applications as gene-specific therapeutics.

Using siRNA technology, the inventors have established that four other genes involved in DNA repair (MUTYH, PNKP, POLD1, and RUVBL2) and two genes encoding P450 cytochrom isoforms (CYP2A6 and CYP4B1) are also involved in astrocytomas chemoresistance. In addition, the inventors have established, for the first time that ERCC2 is functionally involved in drug resistance.

MUTYH which belongs to the Base Excision Repair (BER) system is known to repair 8-oxo-7,8-dihydro-2'deoxyguanosine (8-oxodG) caused by oxidation. MUTYH mutations and variants were associated with development of multiple colorectal adenomas and cancers (Chow et al., Lancet Oncol., 2004, 5, 600-606). PNKP, also belonging to the BER system, was shown to be involved in repairing DNA strand breaks caused by reactive oxygen species, ionizing radiations or alkylating agents (Whitehouse et al., Cell, 2001, 104, 107-117; Chappell et al., EMBO J., 2002, 21, 2827-2832). It has been related to susceptibility to genotoxic agents but not to chemoresistance (Rasouli-Nia et al., P.N.A.S., 2004, 101, 6905-6910). POLD1 is known to be involved in NER and NMR (Nucleotide Mismatch Repair) systems, while RUVBL2 is known to be involved in homologous recombination; these proteins have neither been related to chemosensitivity.

The cytochrome P450 isoforms CYP2A6 and CYP4B1 are known as activators of carcinogenic aromatic amines, and represent possible risk factors for tobacco-related and bladder cancers in human (Kamataki et al., Biochem. Res. Comm., 2005, Sep. 19; Imaoka et al., Biochem. Res. Comm., 2000, 277, 776-780): they have neither been related to chemosensitivity.

The inventors have engineered siRNA which efficiently inhibit the targeted genes expression and significantly sensitize astrocytoma cells to chemotherapy.

These siRNAs are useful as adjuvant in cancer therapy, to sensitize cancer cells to chemotherapy and radiotherapy.

Therefore, the invention relates to a double-stranded short interfering nucleic acid (siNA) molecule comprising a sense and an antisense region, wherein the sense region comprises a nucleotide sequence that is selected from the group consisting of: the sequences SEQ ID NO: 11, 13, 14, 15, 30, 31, 38, 46, 64 and 70 and the sequences having at least 70% identity, preferably at least 80% identity, more preferably at least 90% identity with said sequences, and the antisense region comprises a nucleotide sequence that is complementary to the sense region.

The siNA molecules according to the invention target seven genes (ERCC2, MUTYH, PNKP, POLD1, RUVBL2, CYP2A6 and CYP4B1) of the chromosomic regions 1p32-36 and 19q13.2-4 (loss of heterozygosity regions or LOH region) which are all involved in resistance of cancer cells to chemotherapy and/or radiotherapy. The siNA molecules according to the invention are able to down regulate the expression of the ERCC2, MUTYH, PNKP, POLD1, RUVBL2, CYP2A6 or CYP4B1 genes (target genes) by RNA interference and thereby increase the sensitivity of cancer cells to conventional anticancer agents. Thus the siNA molecules according to the present invention potentiate the cytotoxic effect of chemotherapy/radiotherapy on cancer cells.

The resistance of cancer cells to an anticancer agent may be evaluated by a resistance index (RI) corresponding to the proportion of a cell population that survived to treatment with said anticancer agent. It is calculated as follows: cell number with anticancer agent treatment/cell number in control condition.

The sensibilization effect mediated by the siNA according to the present invention, may be evaluated by the siNA-induced drug sensibilization index (DS) which corresponds to the cell population (%) that survived to a simple treatment with an anticancer agent but died in response to the same treatment with an siNA transfection. It is calculated as follows: (RI control siNA−RItarget siNA)/RIcontrol siNA×100; the target siNA is directed to the resistance gene and the control siNA is directed to a gene which is not involved in resistance to anticancer therapy.

Both indexes may be determined by any assay that measures cell viability, which is well-known in the art, such as for example a MTT assay.

Confirmation that the sensitization effect is mediated by inhibition of the target gene expression may be assayed by any RNA or protein analysis technique, which is well-known in the art (Northern-blot, Western-blot, quantitative RT-PCR).

The siNA molecules according to the invention are defined by reference to the human ERCC2, MUTYH, PNKP, POLD1, RUVBL2, CYP2A6 or CYP4B1 gene sequences (Table I); the target sequence corresponds to the portion of the mRNA which is complementary to the antisense region of the siNA molecule.

TABLE I

Genes targeted with the SiNA

| Target gene | GenBank accession number | Target sequence | positions |
| --- | --- | --- | --- |
| ERCC2 | NM_000400 | SEQ ID NO: 11 | 415-433 |
|  |  | SEQ ID NO: 13 | 1278-1296 |
|  |  | SEQ ID NO: 14 | 1719-1737 |
|  |  | SEO ID NO: 15 | 1978-1996 |
| MUTYH | NM_012222 | SEQ ID NO: 30 | 1475-1493 |
| PNKP | NM_007254 | SEQ ID NO: 31 | 379-397 |
| POLD1 | NM_002691 | SEQ I NO: 38 | 1231-1249 |
| RUVBL2 | NM_006666 | SEQ ID NO: 46 | 335-353 |
| CYP2A6 | NM_000762 | SEQ ID NO: 64 | 591-609 |
| CYP4B1 | NM_000779 | SEQ ID NO: 70 | 645-663 |

The invention encompasses the synthetic, semi-synthetic or recombinant siNA which inhibit the expression of a target gene from any organism. Given the positions of the targets in the human mRNAs, one skilled in the art will easily find the corresponding positions in the homologous sequences of other organisms (eukaryotes, for example mammals) which are accessible in the databases such as the NCBI database (http://www.ncbi.nlm.nih.gov/). Such homologous sequences can be identified as is known in the art, for example using sequence alignment. In addition, the siNA molecule of the invention may inhibit the expression of target gene variants, for example polymorphic variants resulting from haplotype polymorphism.

siNA molecules can be designed to target such homologous sequences, for example using perfectly complementary sequences or by incorporating non-canonical base pairs, for example mismatches and/or wobble base pairs, including flipped mismatches, single hydrogen bond mismatches, trans-type mismatches, triple base interactions and quadruple base interactions, that can provide additional target sequences. For example, the siNA molecule can be designed to target a sequence that is unique to a specific target gene mRNA sequence (a single allele or single nucleotide polymorphism (SNP)) due to the high degree of specificity that the siNA molecule requires, to mediate RNA activity. Alternatively, when mismatches are identified, non-canonical base-pairs (for example mismatches and/or wobble bases) can be used to generate siNA molecules that target more than one sequence. In a non-limiting example, non-canonical base-pairs such as uu and cc base pairs are used to generate siNA molecules that are capable of targeting homologous target gene sequences. In this approach, a single siNA can be used to inhibit expression of more than one gene instead of using more than one siNA molecule to target the different genes.

DEFINITIONS

"short nucleic acid molecule" refers to a nucleic acid molecule no more than 100 nucleotides in length, preferably no more than 80 nucleotides in length, and most preferably, no more than 50 nucleotides in length.

"interfering nucleic acid molecule" refers to a nucleic acid molecule capable of mediating RNA interference.

"RNA interference" (RNAi) refers to the process of sequence specific post-transcriptional gene silencing, induced by introduction of duplexes of synthetic short nucleic acid molecule in cells, for example duplexes of synthetic 21-nucleotide RNAs, as first described by Elbashir et al., Nature 2001, 411, 494- and in the International PCT Application WO 01/75164.

"nucleotide" refers to standard ribonucleotides and deoxyribonucleotides including natural bases (adenine, cytosine, guanine, thymine or uracil) and modified nucleotides that are modified at the sugar, phosphate, and/or base moiety.

"Identity" refers to sequence identity between two nucleic acid molecules. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

"homologous" refers to a nucleic acid molecule having enough identity to another one to lead to RNAi activity, more particularly having at least 70% identity, preferably 80% identity and more preferably 90%.

"complementary" refers to the ability of a nucleic acid to form hydrogen bond(s) by either traditional Watson-Crick base-pairing or other non-traditional type base-pairing. In reference to the nucleic acid molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well-known in the art (see, e.g., Turner et al., 1987, CSH Symp. Quant. Biol., 1987, LII, pp 123-133, Frier et al., P.N.A.S., 1986, 83, 9373-9377; Turner at al., J. Am. Chem. Soc., 1987, 109, 3783-3785). A percent complementarity indicates the percentage of contiguous residues in a nucleic acid molecule that can form hydrogen bonds (e.g., Watson-Crick base-pairing) with a second nucleic acid sequence (e.g., 5, 6, 7, 8, 9, or 10 nucleotides out of a total of 10 nucleotides, in the first oligonucleotide being base-paired to a second nucleic acid sequence having 10 nucleotides represents 50%, 60%, 70%, 80%, 90% and 100% complementarity, respectively). "Perfectly complementary" means that all the contiguous residues of a nucleic acid sequence will hydrogen bond with the same number of contiguous residues in a second nucleic acid sequence.

"target gene" refers to a gene whose expression is to be down-regulated, e.g. ERCC2, MUTYH, PNKP, POLD1, RUVBL2, CYP2A6 or CYP4B1 gene.

"vector" refers to a nucleic acid molecule capable of transporting another nucleic acid to which it has been linked.

"anticancer agent", "anticancer therapy" refers to both chemotherapy using cytotoxic agents and radiotherapy.

In one embodiment, the invention features an siNA molecule wherein each strand comprises or consists of 15 to about 30 (e.g. about 15, 16, 17, 18, 19, 20, 21, 22, 23, 24, 25, 26, 27, 28, 29, or 30) nucleotides, and each strand comprises at least 15 to about 30 (e.g. about 15, 16, 17, 18, 19, 20, 21, 22, 23, 24, 25, 26, 27, 28, 29, or 30 nucleotides) nucleotides that are complementary to the nucleotides of the other strand. For example, the siNA molecule of the invention comprises or consists of a 19 to 21-nucleotide duplex (19 to 21 base pairs).

In another embodiment, the invention features an siNA molecule wherein the sense region comprises or consists of a nucleotide sequence having any of SEQ ID NO: 11, 13, 14, 15, 30, 31, 38, 46, 64 and 70 and the antisense region comprises or consists of a nucleotide sequence having any of SEQ ID NO: 93 to 102, respectively. These siNA target the human genes (Table II).

TABLE II siNA targeting the human genes

| Target gene | siNA sense strand Identification number | siNA antisense strand Identification number | sequence |
|---|---|---|---|
| ERCC2 | SEQ ID NO: 11 | SEQ ID NO: 93 | 5'-gcauuuccaucgacgucc-3' |
|  | SEQ ID NO: 13 | SEQ ID NO: 94 | 5'-ucaaagggcucgaugauga-3' |
|  | SEQ ID NO: 14 | SEQ ID NO: 95 | 5'-auaaagagcagcuuguucc-3' |
|  | SEQ ID NO: 15 | SEQ ID NO: 96 | 5'-aucgaagguaagaaaguca-3' |
| MUTYH | SEQ ID NO: 30 | SEQ ID NO: 97 | 5'-auauacuugauaugucagc-3' |
| PNKP | SEQ ID NO: 31 | SEQ ID NO: 98 | 5'-auugaccaaauacagugug-3' |
| POLD1 | SEQ I NO: 38 | SEQ ID NO: 99 | 5'-uggauguuguaaccgguga-3' |
| RUVBL2 | SEQ ID NO: 46 | SEQ ID NO: 100 | 5'-ucaucuccagggagaagau-3' |

TABLE II-continued siNA targeting the human genes

| | siNA sense strand | siNA antisense strand | |
|---|---|---|---|
| Target gene | identification number | Identification number | sequence |
| CYP2A6 | SEQ ID NO: 64 | SEQ ID NO: 101 | 5'-ugacaggaacucuuugucc-3' |
| CYP4B1 | SEQ ID NO: 70 | SEQ ID NO: 102 | 5'-aucgcugacugcaagguag-3' |

In another embodiment of the invention, the siNA molecule comprises overhanging nucleotide(s) at one or both end(s), preferably, 1 to about 3 (e.g. about 1, 2, or 3) overhanging nucleotides. The overhanging nucleotides which are advantageously at the 3' end of each strand, are preferably 2'-deoxynucleotide(s), preferably 2'deoxypyrimidine(s), such as a 2'-deoxythymidine(s). For example, the siNA molecule of the invention is a 19 to 21-nucleotide duplex, with 19 to 21 base pairs with 3'-terminal tt overhang(s).

In another embodiment of the invention, the siNA molecule comprises blunt end(s), where both ends are blunt, or alternatively, where one of the ends is blunt.

In another embodiment of the invention, the siNA molecule is assembled from two separate oligonucleotide fragments or strands, wherein one fragment (sense strand) comprises the sense region and the second fragment (antisense strand) comprises the antisense region of the siNA molecule.

In another embodiment, the invention features an siNA molecule wherein the sense region is connected to the antisense region via a linker molecule, such as a nucleotide or non-nucleotide linker. A nucleotide linker can be a linker of at least 2 nucleotides in length, for example about 3, 4, 5, 6, 7, 8, 9, or 10 nucleotides in length. Examples of such siNA molecules include small hairpin nucleic acid (shNA) molecules.

A non-nucleotide linker comprises abasic nucleotides, aptamers, polyether, polyamine, polyamide, peptide, carbohydrate, lipid, polyhydrocarbon, or other polymeric compounds.

In another embodiment of the invention, the siNA molecule comprises mismatches, bulges, loops or wobble base pairs to modulate the activity of the siNA molecule to mediate RNA interference.

In another embodiment of the invention, the siNA molecule comprises or consists of ribonucleotide(s) (2'-OH nucleotides).

In addition, the siNA molecule may include one or more modifications which increase resistance to nuclease degradation in vivo and/or improve cellular uptake. The siNA may include nucleotides which are modified at the sugar, phosphate, and/or base moiety, and/or modifications of the 5' or 3' end(s), or the internucleotidic linkage.

In another embodiment of the invention, the siNA molecule comprises one or more modified pyrimidine and/or purine nucleotides, preferably on each strand of the double-stranded siNA. More preferably, said modified nucleotides are selected from the group consisting of: 2'-O-methylnucleotides, 2'-O-methoxyethylnucleotides, deoxynucleotides, such as 2'-deoxynucleotides and 2'-deoxy-2'-fluoronucleotides, universal base nucleotides, acyclic nucleotides and 5-C-methyl nucleotides. An siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA molecule. The percent modification can be based upon the total number of nucleotides present in the sense strand, antisense strand or both the sense and the antisense strands.

In another embodiment, the invention features an siNA molecule wherein the strand comprising the sense region (sense strand) includes a terminal cap moiety at the 5'-end, the 3'-end, or both the 5' and 3' ends of the strand, preferably a deoxy abasic moiety or glyceryl moiety.

In another embodiment, the invention features an siNA molecule wherein the strand comprising said antisense region (antisense strand) includes a phosphate group at the 5'-end.

In another embodiment of the invention, the siNA molecule comprises at least one modified internucleotidic linkage, such as a phosphorothioate linkage.

The siNA molecules according to the invention may be produced by chemical synthesis by using well-known oligonucleotides synthesis methods which make use of common nucleic acid protecting and coupling groups, such as dimethoxytrityl at the 5'-end and phosphoramidites, at the 3' end. The nucleic acid molecules of the present invention can be modified to enhance stability by modification with nuclease resistant groups, for example 2'-amino, 2'-C-allyl, 2'-fluoro, 2'-O-methyl, 2'-H (for a review see Usman and Cedergren, TIBS, 1992, 17, 34 and Usman et al., Nucleic Acids Symp. Ser., 1994, 31, 163). Examples of such modified oligonucleotides include with no limitation: 2' F-CTP, 2' F-UTP, 2' NH2-CTP, 2' NH2-UTP, 2' N3-CTP, 2-thio CTP, 2-thio UTP, 4-thio UTP, 5-iodo CTP, 5-iodo UTP, 5-bromo UTP, 2-chloro ATP, adenosine 5'-(1-thiotriphosphate), cytidine 5'-(1-thiotriphosphate), guanosine-5'-(1-thiotriphosphate), uridine-5'-(1-thiotriphosphate), pseudo-UTP, 5-(3-aminoallyl)-UTP and 5-(3-aminoallyl)-dUTP. siNA contructs can be purified by gel electrophoresis using general methods or can be purified by high pressure liquid chromatography (HPLC) and re-suspended in water.

The chemically-synthesized siNA molecule according to the invention may be assembled from two distinct oligonucleotides which are synthesized separately. Alternatively, both strands of the siNA molecule may be synthesized in tandem using a cleavable linker, for example a succinyl-based linker.

Alternatively, the siNA molecules of the invention may be expressed (in vitro or in vivo) from transcription units inserted into DNA or RNA vectors known to those skilled in the art and commercially available.

The invention relates also to a transcription unit comprising: a transcription initiation region, a transcription termination region, and a nucleic acid sequence encoding at least one siNA molecule according to the present invention, wherein said nucleic acid sequence is operably linked to said initiation region in a manner that allows expression and/or delivery of the siNA molecule.

The nucleic acid sequence may encode one or both strands of the siNA molecule, or a single self-complementary strand that self-hybridizes into an siNA duplex.

The transcription initiation region may be from a promoter for a eukaryotic RNA polymerase I, II or III (pol I, II or III). Transcripts from pol II or pol II promoters are expressed at high levels in all cells. Alternatively, prokaryotic RNA polymerase promoters may be used, providing that prokaryotic RNA polymerase enzyme is expressed in the appropriate cells. Transcription units derived from genes encoding U6 small nuclear transfer RNA and adenovirus VA RNA are useful in generating high concentrations of desired siNA in cells.

The invention concerns also an expression vector comprising a nucleic acid encoding at least one siNA molecule of the instant invention. The expression vector may encode one or both strands of the siNA molecule, or a single self-complementary strand that self-hybridizes into an siNA duplex. The nucleic acid encoding the siNA molecule of the instant invention is preferably inserted in a transcription unit as defined above.

Large numbers of DNA or RNA vectors suitable for siNA molecule expression are known to those of skill in the art and commercially available. The recombinant vectors can be DNA plasmids or viral vectors. SiNA expressing viral vectors can be constructed based on, but not limited to, adeno-associated virus, retrovirus, adenovirus or alphavirus. The recombinant vectors capable of expressing the siNA molecules can be delivered in vivo, and persist in target cells. Alternatively, viral vectors can be used to provide transient expression of siNA molecules.

The invention concerns also eukaryotic or prokaryotic cells which are modified by a vector as defined above.

The invention concerns also a pharmaceutical composition comprising at least an siNA molecule or an expression vector, as defined above, in an acceptable carrier, such as stabilizer, buffer and the like.

A pharmaceutical composition or formulation refers to a form suitable for administration, e.g., systemic or local administration, into a cell or subject, including for example a human. Suitable forms, in part, depend upon the use or the route of entry, for example oral, inhalation, or by injection. These compositions or formulations are prepared according to any method known in the art for the manufacture of pharmaceutical compositions.

In one embodiment, the invention features a composition wherein the siNA molecule or vector is associated to a compound that allows the delivery of the siNA/vector into cancer cells. The compound may be a membrane peptide, transporter, lipid, hydrophobic moiety, cationic polymer, PEI. Examples of membrane peptides include those able to cross the blood-brain barrier, such as with no limitation the Pep: Trans< > (http://www.syntem.com/english/techpeptrans.html). Preferably, the siNA and the compound are formulated in microspheres, nanoparticules or liposomes. Furthermore, the siNA molecule or vector may be associated with a compound that allows a specific targeting of the tumor, such as a ligand of a cell-surface antigen or receptor, for example a peptide or an antibody specific for said antigen/receptor (e.g., PS100, PDGFR, erb-B2).

In another embodiment, the invention features a composition comprising a combination of at least two different siNA molecules.

In another embodiment, the invention features a composition wherein the siNA molecule or vector is associated with at least one anticancer drug.

The invention also concerns an siNA molecule or a vector as defined above, as a medicament.

The invention concerns also the use of an siNA molecule or a vector as defined above, for the manufacture of a medicament for treating cancer.

The cancer may be of any type. Preferably, the cancer is a solid tumor, for example brain tumors such as astrocytomas, glioblastomas, oligodendrogliomas or mixed tumors.

In one embodiment of said use, the siNA molecule or vector is associated with an anticancer drug.

The invention concerns also a product containing at least one siNA molecule or vector as defined above, and an anticancer drug, as a combined preparation for simultaneous, separate or sequential use in anticancer therapy.

The anticancer drugs which are used in combination with the siNA molecule or the vector according to the invention are those commonly used in chemotherapy, and include cytotoxic agents, such as alkylating agents and antimetabolites.

Preferred anticancer drugs are alkylating agents, such as: cisplatin (cis-diaminedichloroplatinum, CDDP or DDP), temozolomide, fotemustine, procarbazine, lomustine and vincristine.

In addition, the siNA molecule according to the invention may be used in combination with other conventional anticancer therapies including radiotherapy, immunotherapy and surgery.

A pharmaceutically effective dose is that dose required to prevent, inhibit the occurrence or treat (alleviate a symptom to some extent, preferably all the symptoms) of a disease or state. The pharmaceutically effective dose of the siNA depends upon the type of cancer, the composition used, the route of administration, the type of mammal being treated, the physical characteristics of the specific mammal under consideration, concurrent medication, and other factors, that those skilled in the medical arts will recognize. Generally, an amount between 0.1 mg/kg and 100 mg/kg body weight/day of active ingredients is administered.

The siNA of the invention may be administered by a single or multiple route(s) chosen from: local (intratumoral, for example intracerebral (intrathecal, intraventricular)), parenteral (percutaneous, subcutaneous, intravenous, intramuscular, intraperitoneal), oral, sub-lingual, or inhalation.

When the siNA molecule or vector is used in combination with chemotherapy or radiotherapy, it is preferably administered immediately prior to the anticancer agent or several hours (2 to 48 hours) before.

In addition to the preceding features, the invention further comprises other features which will emerge from the description which follows, which refers to examples illustrating the siNA molecules and their uses according to the invention, as well as to the appended drawings in which:

FIG. 1 illustrates the screening of DNA-repair genes in human glioma (GHD cells). Cells were seeded in 96-well plates, transfected with siRNA after 24 h and treated with Cisplatin (CDDP) after 48 h. 96 hours post treatment, alive cell number was evaluated with MTT. 1: ERCC2, 2: RAD54L, 3: LIG1, 4: MUTYH 5: PNKP, 6: POLD1, 7: REV7(MAD2L2), 8: MGC13170, 9: RUVBL2, G: GFP. The proportion of a cell population that survives to chemotherapy is evaluated by the chemoresistance index (CI): cell number (OD) with chemotherapy/cell number (OD) in control condition. CI for each siRNA was compared with control CI (siRNA GFP). Data represented the mean of 3 independent experiments. CI is inferior to CIGFP (0.5 or 50%) when siRNA transfection improves chemosensitivity and superior to CIGFP (grey) when it increases chemoresistance. White square corresponds to siRNA with low toxicity (<35% cell death without cisplatin) and with chemosensitization properties.

Figure 2:
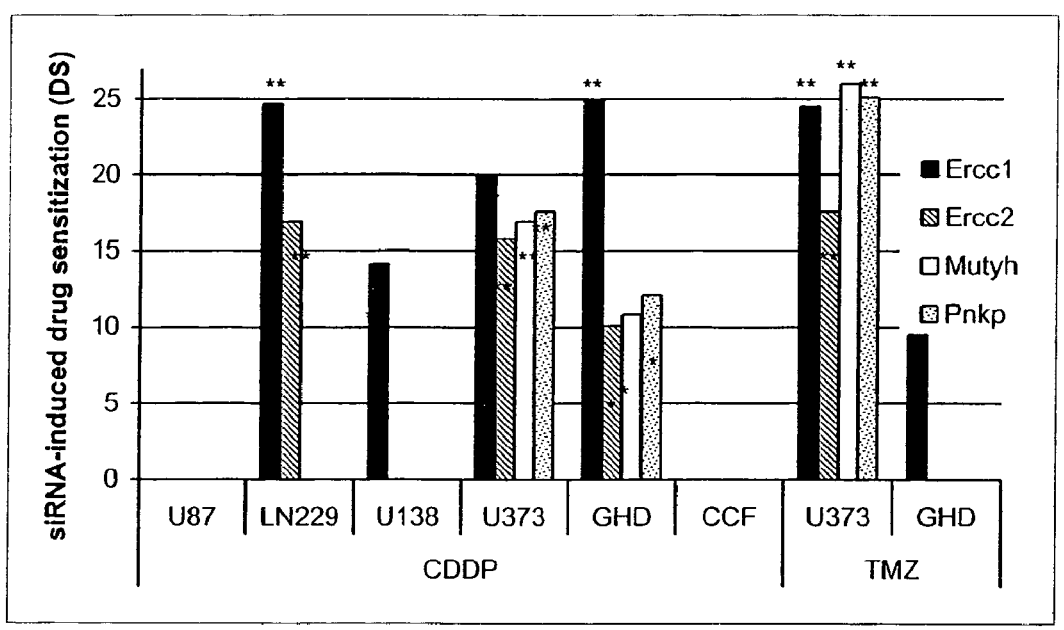

FIG. 2 illustrates drug sensitization by siRNAs targeting four DNA repair genes: ERCC1, ERCC2, MUTYH, and PNKP. SiRNAs were transfected in 6 different astrocytoma derived cell lines treated with CDDP or temozolomide (TMZ). DS corresponds to chemosensitivity induced by siRNA. siRNA targeting ERCC1 was included for comparison. Data represented the mean of 3 independent experiments. Only significant results were reported (*p<0.05; **p<0.01).

Figure 3:
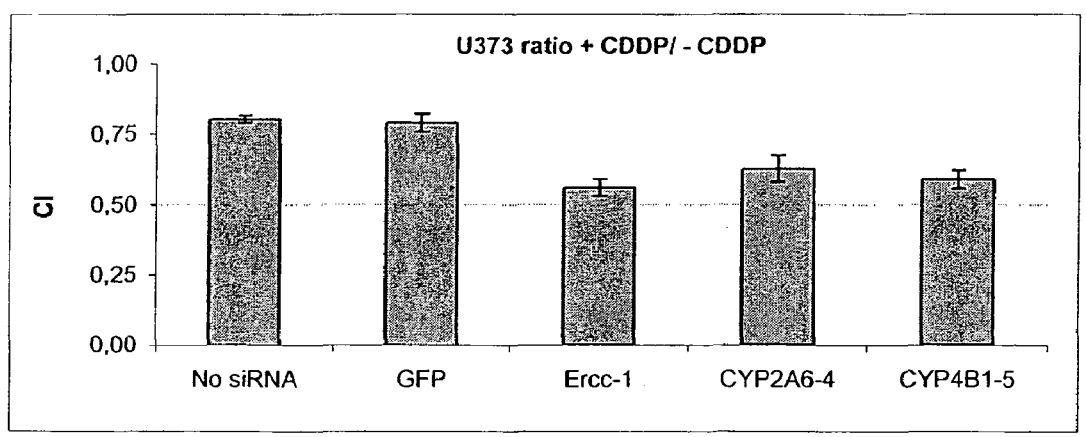

FIG. 3 illustrates the effect of siRNAs targeting two cytochrome P450 isoforms (CYP2A6 and CYP4B1) on the chemosensitization of astrocytoma cells. SiRNAs were transfected in U373 cell line treated with CDDP. The chemoresistance indice (CI) for each siRNA was compared with control CI (siRNA GFP). siRNA targeting ERCC1 was included for comparison. Data represented the mean of 3 independent experiments.

EXAMPLE 1 siRNA Directed to 1p/19q DNA Repair Genes are Able to Sensitize Cancer Cells to Chemotherapy 1) Material and Methods
a) Cell Culture U87, U373, U138, CCF and LN229 cells deriving from human astrocytoma were purchased from American Type Culture Collection (ATCC). GHD cell line derived from a human astrocytoma biopsy, was checked by fluorescence in situ hybridization, chromosome 7 polysomy, chromosome 10 monosomy and immuno-histo-chemistry. Cells were maintained in DMEM (CAMBREX BIOSCIENCES), 10% FCS (v/v; ABCYS), and incubated in a humidified atmosphere with 5% CO2, at 37 deg. C.
b) Inhibition of Gene Expression with siRNA Three to five siRNA pairs were designed for each candidate gene and prepared into duplex form (EUROGENTEC). siRNAs targeting the Green Fluorescent Protein (GFP) and the ERCC 1 protein were used as control siRNAs. 24 hours after cell seeding (96 well plates), siRNA (150 nM) were transfected with Oligofectamine<> (Invitrogen), according to the manufacturer's instructions. Each condition (siRNA) was tested in 3 independent experiments, each time in hexaplicate.

c) Cell Survival and Chemoresistance

Cells were seeded in 96 well plates, transfected with siRNA after 24 h and treated with cisplatine (CDDP, MERCK, 5 M final concentration) or temozolomide (TMZ, SCHERING-PLOUGH, 1 M final concentration) after 48 h. Cell survival was determined 96 hours post-treatment, by measuring mitochondrial succinate dehydrogenase activity, with 3-[4,5-dimethylthiazol-2-yl]-2,5-diphenyltetrazolium bromide (MTT, SIGMA) added to a final concentration of 0.5 mg/ml into culture medium. Culture medium was discarded after 4 h of incubation with MTT and formazan crystals were dissolved in DMSO/ethanol (50/50, v/v). Optical density was read at 540 nm. Chemoresistance was related to an index (CI) corresponding to the proportion of a cell population that survived to chemotherapy. It was calculated as follows: cell number (OD) with chemotherapy/cell number (OD) in control condition. The benefit of siRNA transfection was represented by the siRNA-induced drug sensibilization index (DS) which corresponds to the cell population (%) that survived to a simple chemotherapy treatment but died in response to the same treatment with a siRNA transfection. It was calculated as follows: (CI siRNA GFP−CI siRNAx)/CI SiRNA GFP× 100. Significant differences between series were tested by ANOVA with Statview (SAS institute). Differences were considered significant when p<0.05 (*) and very significant when p<0.01 (**).

d) Q-RT PCR

RNAs were extracted on silica column (Nucleospin< >, MACHEREY-NAGEL). RNAs were reverse transcribed using the M-MLV reverse transcriptase RNase H minus enzyme (Promega) and oligodT as a primer, at 40 deg. C. during 1.5 hours. After reverse transcription, cDNAs were purified (Mini Elute, PCR Purification Kit<>, QIAGEN) and assayed by quantitative PCR using the HotStar Reaction mix (ROCHE), using a pair of primers specific for the candidate gene and the reference gene ERCC1 (Table III). Measurements were carried out on a Light Cycler thermo-cycler (ROCHE).

TABLE III qRT-PCR primers sequences

| Gene | Primer | Sequence (5'-3') | SEQ ID NO: | Annealing temperature (deg. C.) | product size (bp) |
|---|---|---|---|---|---|
| Cyclophyline A | Forward | ttcatctgcactgccaagac | 1 | 61.8 | 158 |
|  | Reverse | tcgagttgtcacagtcagc | 2 |  |  |
| ERCC1 | Forward | ggcgacgtaattcccgacta | 3 | 61.8 | 121 |
|  | Reverse | agttcttccccaggctctgc | 4 |  |  |
| ERCC2 | Forward | cggaactatgggaacctcct | 5 | 64.0 | 200 |
|  | Reverse | tacttctccagggcgacact | 6 |  |  |
| MUTYH | Forward | gtcctgacgtggaggagtgt | 7 | 64.0 | 200 |
|  | Reverse | cctctgcaccagcagaattt | 8 |  |  |
| PNKP | Forward | tcgagagatgacggactcct | 9 | 64.0 | 206 |
|  | Reverse | tttattgtggaggggagctg | 10 |  |  |

Measures were performed twice from each cell sample, and results were expressed as the mean of at least three independent samples (originating from independent in vitro experiments).

2) Results a) Identification of DNA Repair Genes Potentially Involved in Chemoresistance of Astrocytoma Cells Genes potentially responsible for chemoresistance of astrocytoma, were screened from the chromosomic area commonly considered as correlated with oligodendroglioma chemosensitivity (1p36-1p32 and 19q13.2-19q13.4; Smith et al., Oncogene, 1999; 18, 4144-4152). Gene sequences were retrieved from data bases on the web (http://www.ncbi.nlm.nih.gov/PubMed/; http://www.ensembl.org; http://www.c-gal.icnet.uk/DNA Repair Genes.html; Supplement to the paper by Wood et al., Mutat. Res., 2005, 577, 275-283) and published data (Harris, A. L., Int J Radiat Biol Relat Stud Phys Chem Med, 1985, 48, 675-90; Christmann et al., Toxicology, 2003, 193, 3-34; Wood et al., Mutat. Res., 2005, 577, 275-283). Eight genes belonging to different repair systems were selected (Table IV).

TABLE IV

List of DNA repair-associated genes located 1p/19q LOH regions

| DNA repair genes | DNA repair system | Accession number | Localization |
|---|---|---|---|
| LIG1 | NER | NM_000234 | 19q13.2-3 |
| ERCC2 (XPD) | NER | NM_000400 | 19q 13.3 |
| POLD1 | NER and MMR** | NM_002691 | 19q13.3 |
| RUVBL2 | Homologous Recombination | NM_006666 | 19q13.3 |
| PNKP | BER*** | NM_007254 | 19q13.3-4 |
| RAD 54L | Homologous Recombination | NM_003579 | 1p32 |
| MUTYH | BER | NM_012222 | 1p34.3 |
| MAD2L2 (REV7) | DNA polymerase | NM 006341 | 1p36 |

*NER: Nucleotide Excision Repair
**NMR: Nucleotide Mismatch repair
***BER: Base excision repair b) In Vitro Chemosensitivity Assay An in vitro assay for the siRNAs high-throughput screening, was developed to find out which genes (Table IV) are implicated in glioma chemoresistance mechanisms. The cell number after chemotherapy and siRNA transfection was measured to have a global chemosensitization evaluation, defined as a significant increased cell death compared with the effect of the drug alone. In a first series of experiments, the following conditions of the assay were established: (i) drug and siRNA treatment protocols, (ii) specific temporal sequence of cell seeding and drug treatment, (iii) siRNA transfection, (iii) cell viability measurement. CDDP was chosen because it is an alkylating agent harboring a very reproducible activity in vitro. Most, if not all, cell damages occurred during the first hour of drug treatment since one and 24 hour(s) incubations were equally efficient. Moreover, it was established that the mRNA amount was the lowest 24 and 48 hours after siRNA transfection. Altogether, these data suggested that siRNAs had to be added prior to the drug.

c) Screening of DNA-Repair Genes Involved in Chemoresistance of Astrocytoma Cells The screening was performed in three steps. First siRNAs targeting candidate genes were screened on one cell line and results were confirmed at statistic level in further experiments. The study was then extended to six astrocytoma-derived cell lines and the siRNAs were validated at molecular level. Finally, the study was extended to a second chemotherapy agent.

The eight DNA-repair genes located in the 1p/19q (Table IV) were screened with five different siRNAs by gene, on the GHD cell line. The siRNAs sequences are presented in Table V. One siRNA specific for GFP and one siRNA specific for ERCC1 were used as controls.

TABLE V

SiRNAs sequences

| Gene | siRNA sequence*(1) (2) | SEQ ID NO: |
|---|---|---|
| ERCC2 | 5'-ggacgucgaugggaaaugc-3' | 11 |
| | 5'-agacggugcucaggaucaa-3' | 12 |
| | 5'-ucaucaucgagcccuuuga-3' | 13 |
| | 5'-ggaacaagcugcucuuuau-3' | 14 |
| | 5'-ugacuuucuuaccuucgau-3' | 15 |
| LIG1 | 5'-agacgcucagcagcuucuu-3' | 16 |
| | 5'-gaagauagacaucaucaaa-3' | 17 |
| | 5'-agacagcagagcccagaaa-3' | 18 |
| | 5'-gcagacguucugcgagguu-3' | 19 |
| | 5'-gcagauccagccauuccaa-3' | 20 |
| MAD2L2 | 5'-gaagaaugauguggagaaa-3' | 21 |
| | 5'-gacucgcuguugucucaug-3' | 22 |
| | 5'-cucgcaacaugcagaagau-3' | 23 |
| | 5'-gaagauccaggucaucaag-3' | 24 |
| | 5'-ugagcaggaugaccacaug-3' | 25 |
| MUTYH | 5'-gaagcaugcuaagaacaac-3' | 26 |
| | 5'-ugggaugauugcugagugu-3' | 27 |
| | 5'-gcaccuuguuucccagca-3' | 28 |
| | 5'-gguuguccacaccuucucu-3' | 29 |
| | 5'-gcugacauaucaaguauau-3' | 30--> |
| PNKP | 5'-cacacuguauuuggucaau-3' | 31 |
| | 5'-agagacccgcacaccagaa-3' | 32 |
| | 5'-gaaucuuugacccagagau-3' | 33 |
| | 5'-aguccaccuuucucaagaa-3' | 34 |
| | 5'-caaccgguuucgagagaug-3' | 35 |
| POLD1 | 5'-ggagauggaggcagaacac-3' | 36 |
| | 5'-guuggagauugaccauuau-3 | 37 |
| | 5'-ucaccgguuacaacaucca-3' | 38 |
| | 5'-cuuagacuccaccagcugc-3' | 39 |
| | 5'-auucagauggauaccucc-3' | 40 |
| RAD54L | 5'-ccagcauugugaauagaug-3' | 41 |
| | 5'-ucaccucgcuaaagaagcu-3' | 42 |
| | 5'-ggagcuguuuauccuggau-3' | 43 |
| | 5'-ugaucugcuuagauauuuc-3' | 44 |
| | 5'-gcagugagacccagaucca-3' | 45 |
| RUVBL2 | 5'-aucuucucccuggagauga-3' | 46 |
| | 5'-acugacccucaagaccaca-3' | 47 |
| | 5'-acgcaagggguacagaagug-3' | 48 |
| GFP | 5'-gacguaaacggccacaaguuc-3' | 49 |
| ERCCI | 5'-ggagcuggcuaagaugugu-3' | 50 |

(1) siRNA sequences are defined by the sequence of the sense strand. The antisense strand is perfectly complementary to the sense strand. SiRNAs responsible for a significant sensitization effect are in bold.
(2) Said sequences comprise a 3'-terminal tt overhang.

Cell viability was measured in absence and in presence of CDDP. SiRNAs were selected on the basis of two criteria: the absence of basal toxicity and their efficiency to improve chemotherapy treatment. Toxic siRNAs inducing more than 35% cell death after transfection (without CDDP) were discarded. In contrast, those increasing cell death were retained. An siRNA increased chemosensitivity when its chemoresistance index (CI) was lower than GFP siRNA CI, ie lower than 0.5. In FIG. 1, the white square corresponds to siRNA with low toxicity and with chemo-sensitization properties. Eight siRNAs out of 38 matched with these criteria, corresponding to 5 genes: ERCC2, MUTYH, PNKP, POLD1, and RUVBL2 (FIG. 1). Only one sequence of MUTYH, PNKP, RUVBL2 and POLD1 (SEQ ID NO: 30, 31, 38 and 46) siRNAs increased chemosensitivity while 4 (SEQ ID NO: 11, 13, 14 and 15) out of 5 sequences targeting ERCC2 fulfilled these conditions.

The most efficient siRNA for each of these genes was transfected in 6 different glioma derived cell lines treated with CDDP or temozolomide (TMZ). CIs for each siRNA were compared with control CI (siRNA GFP). The results confirmed that three siRNAs targeting ERCC2, MUTYH and PNKP, respectively, had a significant chemo-sensitization effect on astrocytoma cells (FIG. 2). The three siRNAs were equally efficient (up to 17%) on 3 (ERCC2) or 2 (MUTYH and PNKP) cell lines (FIG. 2). When combined by 2 or 3, siRNAs did not show any greater efficiency. By comparison, inhibition of ERCC1 was more potent to sensitize cells to CDDP (up to 24.9%) and its effect was the most widespread since 4 out of the 6 cell lines were sensitized.

The previously observed effects were validated at molecular level; a significant mRNA content decrease was confirmed by qRT-PCR for all siRNAs (Table VI).

TABLE VI

| Validation of SiRNA- | | | |
| --- | --- | --- | --- |
| Cell line | mRNA | inhibition % | PANOVA |
| GHD | ERCC2 | 61.6 | 0.011 |
|  | MUTYH | 71.0 | 0.004 |
|  | PNKP | 83.8 | 0.005 |
|  | ERCC1 | 58.6 | 0.019 |
| U373 | ERCC2 | 95.7 | 0.003 |
|  | MUTYH | 72.9 | 0.007 |
|  | PNKP | 44.2 | 0.013 |
|  | ERCC1 | 77.4 | 0.018 |

When a particular siRNA was transfected, the quantities in mRNA corresponding to all the other non targetted genes were unchanged, confirming the target specificity of the selected siRNA. There was no obvious link between the efficiency of siRNA to decrease mRNA amounts (nor with final mRNA content) and functional impact on cell viability (FIG. 2). This is reinforced by the observation that ERCC1 mRNA amount actually decreased (by 65%) in U87 cells which were yet not chemosensitized.

d) Study for a Link Between DNA-Repair Genes Expression and siRNA-Induced Chemotherapy Expression of the 4 DNA-repair genes was studied by qRT-PCR in the 6 cell lines, with (induced level) or without cisplatin (basal level) to analyse the hypothesis that differences in expression could account for differences in siRNA responses. For each individual mRNA, the relative gene expression levels were roughly similar in all cell lines in absence of drug (Table VII).

TABLE VII

| DNA repair gene expression | | | | |
| --- | --- | --- | --- | --- |
| Cell line | Basal | | Induced | | |
|  | Qty* | sem | Qty | sem | %** |
| ERCC1 | | | | | |
| GHD | 33 | 13 | 35 | 15 | 104 |
| LN229 | 33 | 13 | 78 | 30 | 233 |
| U138 | 40 | 17 | 97 | 36 | 242 |
| U373 | 11 | 5 | 12 | 6 | 110 |
| U87 | 25 | 10 | 25 | 10 | 99 |
| CCF | 8 | 4 | 12 | 6 | 148 |
| ERCC2 | | | | | |
| GHD | 10 | 3 | 17 | 5 | 163 |
| LN229 | 4 | 1 | 11 | 1 | 268 |
| U138 | 21 | 4 | 66 | 15 | 312 |
| U373 | 14 | 1 | 17 | 4 | 122 |
| U87 | 5 | 1 | 5 | 1 | 96 |

TABLE VII-continued

| DNA repair gene expression | | | | |
| --- | --- | --- | --- | --- |
| Cell line | Basal | | Induced | | |
|  | Qty* | sem | Qty | sem | %** |
| CCF | 2 | 1 | 3 | 1 | 196 |
| MUTYH | | | | | |
| GHD | 108 | 19 | 114 | 14 | 105 |
| LN229 | 137 | 52 | 439 | 44 | 320 |
| U138 | 185 | 43 | 469 | 157 | 254 |
| U373 | 49 | 33 | 135 | 41 | 278 |
| U87 | 91 | 28 | 101 | 37 | 110 |
| CCF | 45 | 20 | 117 | 40 | 257 |
| PNKP | | | | | |
| GHD | 94 | 28 | 83 | 23 | 88 |
| LN229 | 137 | 35 | 283 | 70 | 206 |
| U138 | 550 | 116 | 1198 | 171 | 218 |
| U373 | 115 | 31 | 149 | 4 | 130 |
| U87 | 224 | 50 | 196 | 63 | 88 |
| CCF | 76 | 20 | 130 | 29 | 171 |

*quantity in zeptomol ($10^{<-21>}$ mol) in a 25 ng total RNA extract
**percentage of basal level MUTYH and PNKP mRNAs were the most abundant and ERCC2 was generally the less one. Expression of the four genes was reinforced up to three times in response to chemotherapy, in at least two cell lines (Table VII). No gene was up-regulated in all cell lines, the four genes were up-regulated in two cell lines (LN229 and U138) and none in one other (U87). Thus, there was no common induction profile conserved among all cell lines. Finally, no correlation was found between chemosensitization by a siRNA (DS) and basal or CDDP-induced expression of corresponding gene or even global expression of the 4 genes.

e) Transposition of Chemo-Sensitization by siRNAs from CDDP to Temozolomide.

Since temozolomide is becoming the chemotherapy gold standard for gliomas, the study was extended to this drug. ERCC1 siRNAs were more efficient for sensitizing astrocytoma-derived cell lines to this second drug. However, down-regulating MUTYH, PNKP or ERCC2 improved very significantly drug effects in U373 cells (FIG. 2).

EXAMPLE 2 siRNA Directed to 1p/19q Genes Involved in Drug Metabolism are Able to Sensitize Cancer Cells to Chemotherapy 1) Material and Methods The experimental procedures are described in example 1.

2) Results a) Identification of Genes Potentially Involved in Chemoresistance of Astrocytoma Cells Genes potentially responsible for chemoresistance of astrocytoma, were screened from the chromosomic area considered as commonly correlated with oligodendroglioma chemosensitivity, as described in example 1. Nine genes involved in drug metabolism (detoxification, cellular efflux, apoptosis) were selected (Table VIII).

TABLE VIII

List of drug metabolism-associated genes located on 1p/19q LOH regions

| Genes | Function | Accession number | Localization |
|---|---|---|---|
| CYP2B6 | Drug and lipid metabolism: Cytochrome P450 proteins (monooxygenases) catalyse reactions involved in drug metabolism and synthesis of cholesterol, steroids and other lipids | NM 000767 | 19q13.2 |
| CYP2F1 | | NM 000774 | 19q13.2 |
| CYP2A6 | | NM_000762 | 19q13.2 |
| CYP4B1 | | NM_000779 | 1p34-p12 |
| FRAP1 | Signal transduction: The corresponding protein belongs to the family of phosphatidylinositol kinase-related kinases. These kinases mediate cellular responses to stresses such as DNA damage and nutrient deprivation | NM 004958 | 1p36.2 |
| MGC13170 | Multidrug resistance-related protein: Putative MDR-like function | NM 199249 | 19q13.33 |
| MLP | Signal transduction: The myristoylated, alanine-rich protein MARCKS is a widely expressed, prominent substrate for protein kinase C, involved in brain development | NM_023009 | 1p35.1 |
| MSH4 | DNA metabolism: DNA mismatch repair and meiotic recombination | NM 002440 | 1p31 |
| RPS8 | Translation: Protein participating to translation complex | NM 001012 | 1p34.1-p32 | b) Screening of DNA-Repair Genes Involved in Chemoresistance of Astrocytoma Cells The eight genes located in the 1p/19q (Table VIII) were screened with five different siRNAs by gene, on two different cell-lines, U373 and GHD. The siRNAs sequences are presented in Table IX. A siRNA specific for GFP was used as control.

TABLE IX

SiRNA sequences*

| Gene | siRNA sequence | position | SEQ ID NO: |
|---|---|---|---|
| CYP2B6 | ccaccauccuccagaacuu | 1359 | 51 |
| | ggaaaucaaugcuuacauu | 724 | 52 |
| | acaggugauuggcccacau | 994 | 53 |
| | ugacccacacuacuuugaa | 1198 | 54 |
| | acacgcucucgcucuucu | 879 | 55 |
| | ccagggagaggaguuuagu | 326 | 91 |
| | gaagcauugaggagcgaau | 475 | 92 |
| CYP2F1 | ccacacauaaccugcucuu | 928 | 56 |
| | gcauaagcacagccaucuu | 64 | 57 |
| | ucaaugacaacuuccaaau | 661 | 58 |
| | acacggaguucuacuugaa | 857 | 59 |
| | ccaccgucaugcagaacuu | 1370 | 60 |
| CYP2A6 | ugaccacguugaaccucuu | 887 | 61 |
| | ccaaguuucgggauuucuu | 1142 | 62 |
| | gcaccagcaucguuguaga | 1020 | 63 |
| | ggacaaagaguuccuguca | 591 | 64 |
| | gcaagccugucaccuuugu | 1175 | 65 |
| CYP4B1 | ugagccugacuaugccaaa | 297 | 66 |
| | ugaugugcugaagcccuau | 453 | 67 |
| | ggagucuacucgcuucuau | 253 | 68 |
| | gcacgaucauucuucucau | 3228 | 69 |
| | cuaccuugcagucagcgau | 645 | 70 |
| FRAP1 | agaacugcugauccaaau | 1230 | 71 |
| | ccagcagcauaagcaggaa | 5287 | 72 |
| | caagcgacaucccaugaaa | 7670 | 73 |
| | gcaggcugcucuccauggu | 969 | 74 |
| | ggcucaugcugggacccaa | 1010 | 75 --> |
| MGC13170 | ggagcuguccauacgccac | 1159 | 76 |
| | ggagaagguggauaagugg | 1068 | 77 |
| | ccaggcucaugcugggacc | 1007 | 78 |

TABLE IX-continued

SiRNA sequences*

| Gene | siRNA sequence | position | SEQ ID NO: |
|---|---|---|---|
| | gugcagccucagaagaaga | 674 | 103 |
| | gaagaagaaauucucuuuc | 453 | 104 |
| MLP | cgagggcacugcucaggaa | 597 | 79 |
| | gaagaaauucucuuucaag | 456 | 80 |
| | aaagcaauggagacuuauc | 293 | 81 |
| | cgacuucguucuaauauau | 1089 | 82 |
| | ucaacuuccuucagaauuu | 1694 | 83 |
| MSH4 | guagacgacuucguucuaa | 1084 | 84 |
| | agagcuuacuauggduuccu | 1380 | 85 |
| | agaagguauuggcauuugu | 2345 | 86 |
| | gcugacuccugaggaagaa | 407 | 87 |
| | ccaagacccuggugaagaa | 301 | 105 |
| RPS8 | ccacaagaagcggaaguau | 86 | 88 |
| | agaguuggaguucuaucuu | 602 | 89 |
| | agagaaagcccuaccacaa | 73 | 90 |

*siRNA sequences are defined by the sequence of the sense strand. The antisense strand is perfectly complementary to the sense strand. SiRNAs responsible for a significant sensitization effect are highlighted in bold.

To select siRNAs specifically including a chemosensitive effect, those inducing a basal toxic effect were eliminated (more than 35% cell death after transfection). A positive chemosensitive effect was considered for siRNAs inducing a cytotoxic effect compared to siRNA GFP/CDDP condition. 2 siRNAs out of 45, matched with these criteria, corresponding to 2 genes: CYP2A6 and CYP4B1 (Table IX).

The most efficient siRNA for each of these genes was transfected in 6 different glioma derived cell lines treated with CDDP or temozolomide (TMZ). CIs for each siRNA were compared with control CI (siRNA GFP). The results confirmed that two siRNAs (SEQ ID NO: 64 and 70) targeting CYP2A6 and CYP4B1, respectively, had a significant chemosensitization effect on astrocytoma cells (FIG. 3).

What is claimed is:

1. A double-stranded short interfering nucleic acid molecule comprising a sense region and an antisense region,
    wherein the sense region comprises a nucleotide sequence that is selected from the group consisting of: SEQ ID NO: 64 and SEQ ID NO: 70,
    and the antisense region comprises a nucleotide sequence that is complementary to the sense region.

2. The double-stranded short interfering nucleic acid molecule according to claim 1, wherein each strand of the molecule comprises 15 to about 30 nucleotides, and each strand of the molecule comprises at least 15 to about 30 nucleotides that are complementary to the nucleotides of the other strand.

3. The double-stranded short interfering nucleic acid molecule according to claim 2, wherein the molecule comprises a 19 to 21-nucleotide duplex.

4. The double-stranded short interfering nucleic acid molecule according to claim 1, wherein the sense region comprises the nucleotide sequence of SEQ ID NO: 64 or SEQ ID NO: 70, and the antisense region comprises the nucleotide sequence of SEQ ID NO: 101 or SEQ ID NO: 102, respectively.

5. The double-stranded short interfering nucleic acid molecule according to claim 1, comprising 1 to about 3 overhanging nucleotides at the 3' end of each strand.

6. The double-stranded short interfering nucleic acid molecule according to claim 1, comprising blunt end(s).

7. The double-stranded short interfering nucleic acid molecule according to claim 1, wherein the molecule is assembled from two separate oligonucleotide fragments, and one fragment comprises the sense region and a second fragment comprises the antisense region of the short interfering nucleic acid molecule.

8. The double-stranded short interfering nucleic acid molecule according to claim 1, wherein the sense region is connected to the antisense region via a linker molecule.

9. The double-stranded short interfering nucleic acid molecule according to claim 1, comprising ribonucleotides.

10. The double-stranded short interfering nucleic acid molecule according to claim 1, comprising one or more modified pyrimidine and/or modified purine nucleotides.

11. The double-stranded short interfering nucleic acid molecule according to claim 1, wherein a strand comprising the sense region includes a terminal cap moiety at the 5' and/or 3'-end(s).

12. The double-stranded short interfering nucleic acid molecule according to claim 1, wherein a strand comprising the antisense region includes a phosphate group at the 5'-end.

13. The double-stranded short interfering nucleic acid molecule according to claim 1, comprising at least one modified inter-nucleotide linkage.

14. A transcription unit comprising:
a transcription initiation region;
a transcription termination region; and
a nucleic acid sequence encoding at least one short interfering nucleic acid molecule according to claim 1,
wherein said nucleic acid sequence is operably linked to said transcription initiation region in a manner that allows expression and/or delivery of the short interfering nucleic acid molecule.

15. An expression vector comprising a transcription unit comprising:
a transcription initiation region;
a transcription termination region; and
a nucleic acid sequence encoding at least one short interfering nucleic acid molecule according to claim 1,
wherein said nucleic acid sequence is operably linked to said transcription initiation region in a manner that allows expression and/or delivery of the short interfering nucleic acid molecule.

16. A cell modified by an expression vector comprising a transcription unit comprising:
a transcription initiation region;
a transcription termination region; and
a nucleic acid sequence encoding at least one short interfering nucleic acid molecule according to claim 1,
wherein said nucleic acid sequence is operably linked to said transcription initiation region in a manner that allows expression and/or delivery of the short interfering nucleic acid molecule.

17. A pharmaceutical composition comprising at least:
a short interfering nucleic acid molecule according to claim 1, or
an expression vector comprising a transcription unit, said transcription unit comprising a transcription initiation region, a transcription termination region, and a nucleic acid sequence encoding at least one short interfering nucleic acid molecule according to claim 1, wherein said nucleic acid sequence is operably linked to said transcription initiation region in a manner that allows expression and/or delivery of the short interfering nucleic acid molecule,
in an acceptable carrier.

18. A pharmaceutical composition comprising at least:
a short interfering nucleic acid molecule according to claim 1, or
an expression vector comprising a transcription unit, said transcription unit comprising a transcription initiation region, a transcription termination region, and a nucleic acid sequence encoding at least one short interfering nucleic acid molecule according to claim 1, wherein said nucleic acid sequence is operably linked to said transcription initiation region in a manner that allows expression and/or delivery of the short interfering nucleic acid molecule,
in an acceptable carrier,
the composition comprising a combination of at least two different short interfering nucleic acid molecules.

19. A pharmaceutical composition comprising at least
a short interfering nucleic acid molecule according to claim 1, or
an expression vector comprising a transcription unit, said transcription unit comprising a transcription initiation region, a transcription termination region, and a nucleic acid sequence encoding at least one short interfering nucleic acid molecule according to claim 1, wherein said nucleic acid sequence is operably linked to said transcription initiation region in a manner that allows expression and/or delivery of the short interfering nucleic acid molecule,
in an acceptable carrier,
wherein the short interfering nucleic acid molecule or the expression vector is associated with at least one anticancer drug.

20. The short interfering nucleic acid molecule according to claim 1 as a medicament, in a form to be administered by a single route or by multiple routes selected from local, parenteral, oral, sub-lingual or inhalation.

21. The expression vector according to claim 15 as a medicament, in a form to be administered by a single route or by multiple routes selected from local, parenteral, oral, sub-lingual or inhalation.

22. A method for treating cancer comprising administering to a patient in need thereof:
the short interfering nucleic acid molecule according to claim 1, or
an expression vector comprising a transcription unit, said transcription unit comprising a transcription initiation region, a transcription termination region, and a nucleic acid sequence encoding at least one short interfering nucleic acid molecule according to claim 1, wherein said nucleic acid sequence is operably linked to said transcription initiation region in a manner that allows expression and/or delivery of the short interfering nucleic acid molecule.

* * * * *

SEQUENCE LISTING

<160> NUMBER OF SEQ ID NOS: 105

<210> SEQ ID NO 1
<211> LENGTH: 20
<212> TYPE: DNA
<213> ORGANISM: Artificial sequence
<220> FEATURE:
<223> OTHER INFORMATION: Synthetic Forward primer cyclophyline A

<400> SEQUENCE: 1
ttcatctgca ctgccaagac                                                   20

<210> SEQ ID NO 2
<211> LENGTH: 19
<212> TYPE: DNA
<213> ORGANISM: Artificial sequence
<220> FEATURE:
<223> OTHER INFORMATION: Synthetic Reverse primer cyclophyline A

<400> SEQUENCE: 2
tcgagttgtc acagtcagc                                                    19

<210> SEQ ID NO 3
<211> LENGTH: 20
<212> TYPE: DNA
<213> ORGANISM: Artificial sequence
<220> FEATURE:
<223> OTHER INFORMATION: Synthetic Forward primer ERcc1

<400> SEQUENCE: 3
ggcgacgtaa ttcccgacta                                                   20

<210> SEQ ID NO 4
<211> LENGTH: 20
<212> TYPE: DNA
<213> ORGANISM: Artificial sequence
<220> FEATURE:
<223> OTHER INFORMATION: Synthetic Reverse primer ERCC1

<400> SEQUENCE: 4
agttcttccc caggctctgc                                                   20

<210> SEQ ID NO 5
<211> LENGTH: 20
<212> TYPE: DNA
<213> ORGANISM: Artificial sequence
<220> FEATURE:
<223> OTHER INFORMATION: Synthetic Forward primer ERCC2

<400> SEQUENCE: 5
cggaactatg ggaacctcct                                                   20

<210> SEQ ID NO 6
<211> LENGTH: 20
<212> TYPE: DNA
<213> ORGANISM: Artificial sequence
<220> FEATURE:
<223> OTHER INFORMATION: Synthetic Reverse primer ERCC2

<400> SEQUENCE: 6
tacttctcca gggcgacact                                                   20

<210> SEQ ID NO 7
<211> LENGTH: 20
<212> TYPE: DNA

```
<213> ORGANISM: Artificial sequence
<220> FEATURE:
<223> OTHER INFORMATION: Synthetic Forward primer MUTYH

<400> SEQUENCE: 7
gtcctgacgt ggaggagtgt                                                   20

<210> SEQ ID NO 8
<211> LENGTH: 20
<212> TYPE: DNA
<213> ORGANISM: Artificial sequence
<220> FEATURE:
<223> OTHER INFORMATION: Synthetic Reverse primer MUTYH

<400> SEQUENCE: 8
cctctgcacc agcagaattt                                                   20

<210> SEQ ID NO 9
<211> LENGTH: 20
<212> TYPE: DNA
<213> ORGANISM: Artificial sequence
<220> FEATURE:
<223> OTHER INFORMATION: Synthetic Forward primer PNKP

<400> SEQUENCE: 9
tcgagagatg acggactcct                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic Reverse primer PNKP

<400> SEQUENCE: 10
tttattgtgg aggggagctg                                                   20

<210> SEQ ID NO 11
<211> LENGTH: 19
<212> TYPE: RNA
<213> ORGANISM: Artificial sequence
<220> FEATURE:
<223> OTHER INFORMATION: Synthetic siRNA sequence ERCC2

<400> SEQUENCE: 11
ggacgucgau gggaaaugc                                                    19

<210> SEQ ID NO 12
<211> LENGTH: 19
<212> TYPE: RNA
<213> ORGANISM: Artificial sequence
<220> FEATURE:
<223> OTHER INFORMATION: Synthetic siRNA sequence ERCC2

<400> SEQUENCE: 12
agacggugcu caggaucaa                                                    19

<210> SEQ ID NO 13
<211> LENGTH: 19
<212> TYPE: RNA
<213> ORGANISM: Artificial sequence
<220> FEATURE:
<223> OTHER INFORMATION: Synthetic siRNA sequence ERCC2

<400> SEQUENCE: 13
ucaucaucga gcccuuuga                                                    19
```

```
<210> SEQ ID NO 14
<211> LENGTH: 19
<212> TYPE: RNA
<213> ORGANISM: Artificial sequence
<220> FEATURE:
<223> OTHER INFORMATION: Synthetic siRNA sequence ERCC2

<400> SEQUENCE: 14
ggaacaagcu gcucuuuau                                                    19

<210> SEQ ID NO 15
<211> LENGTH: 19
<212> TYPE: RNA
<213> ORGANISM: Artificial Sequence
<220> FEATURE:
<223> OTHER INFORMATION: Synthetic siRNA sequence ERCC2

<400> SEQUENCE: 15
ugacuuucuu accuucgau                                                    19

<210> SEQ ID NO 16
<211> LENGTH: 19
<212> TYPE: RNA
<213> ORGANISM: Artificial sequence
<220> FEATURE:
<223> OTHER INFORMATION: Synthetic siRNA sequence LIG1

<400> SEQUENCE: 16
agacgcucag cagcuucuu                                                    19

<210> SEQ ID NO 17
<211> LENGTH: 19
<212> TYPE: RNA
<213> ORGANISM: Artificial sequence
<220> FEATURE:
<223> OTHER INFORMATION: Synthetic siRNA sequence LIG1

<400> SEQUENCE: 17
gaagauagac aucaucaaa                                                    19

<210> SEQ ID NO 18
<211> LENGTH: 19
<212> TYPE: RNA
<213> ORGANISM: Artificial sequence
<220> FEATURE:
<223> OTHER INFORMATION: Synthetic siRNA sequence LIG1

<400> SEQUENCE: 18
agacagcaga gcccagaaa                                                    19

<210> SEQ ID NO 19
<211> LENGTH: 19
<212> TYPE: RNA
<213> ORGANISM: Artificial sequence
<220> FEATURE:
<223> OTHER INFORMATION: Synthetic siRNA sequence LIG1

<400> SEQUENCE: 19
gcagacguuc ugcgagguu                                                    19

<210> SEQ ID NO 20
<211> LENGTH: 19
<212> TYPE: RNA
<213> ORGANISM: Artificial sequence
<220> FEATURE:
<223> OTHER INFORMATION: Synthetic siRNA sequence LIG1
```

-continued

```
<400> SEQUENCE: 20
gcagauccag ccauuccaa                                                    19

<210> SEQ ID NO 21
<211> LENGTH: 19
<212> TYPE: RNA
<213> ORGANISM: Artificial sequence
<220> FEATURE:
<223> OTHER INFORMATION: Synthetic siRNA sequence MAD2L2

<400> SEQUENCE: 21
gaagaaugau guggagaaa                                                    19

<210> SEQ ID NO 22
<211> LENGTH: 19
<212> TYPE: RNA
<213> ORGANISM: Artificial sequence
<220> FEATURE:
<223> OTHER INFORMATION: Synthetic siRNA sequence MAD2L2

<400> SEQUENCE: 22
gacucgcugu ugucucaug                                                    19

<210> SEQ ID NO 23
<211> LENGTH: 19
<212> TYPE: RNA
<213> ORGANISM: Artificial sequence
<220> FEATURE:
<223> OTHER INFORMATION: Synthetic siRNA sequence MAD2L2

<400> SEQUENCE: 23
cucgcaacau gcagaagau                                                    19

<210> SEQ ID NO 24
<211> LENGTH: 19
<212> TYPE: RNA
<213> ORGANISM: Artificial sequence
<220> FEATURE:
<223> OTHER INFORMATION: Synthetic siRNA sequence MAD2L2

<400> SEQUENCE: 24
gaagauccag gucaucaag                                                    19

<210> SEQ ID NO 25
<211> LENGTH: 19
<212> TYPE: RNA
<213> ORGANISM: Artificial sequence
<220> FEATURE:
<223> OTHER INFORMATION: Synthetic siRNA sequence MAD2L2

<400> SEQUENCE: 25
ugagcaggau guccacaug                                                    19

<210> SEQ ID NO 26
<211> LENGTH: 19
<212> TYPE: RNA
<213> ORGANISM: Artificial sequence
<220> FEATURE:
<223> OTHER INFORMATION: Synthetic siRNA sequence MUTYH

<400> SEQUENCE: 26
gaagcaugcu aagaacaac                                                    19

<210> SEQ ID NO 27
<211> LENGTH: 19
<212> TYPE: RNA
```

```
<213> ORGANISM: Artificial sequence
<220> FEATURE:
<223> OTHER INFORMATION: Synthetic siRNA sequence MUTYH

<400> SEQUENCE: 27
ugggaugauu gcugagugu                                                19

<210> SEQ ID NO 28
<211> LENGTH: 19
<212> TYPE: RNA
<213> ORGANISM: Artificial sequence
<220> FEATURE:
<223> OTHER INFORMATION: Synthetic siRNA sequence MUTYH

<400> SEQUENCE: 28
gcacccuugu uucccagca                                                19

<210> SEQ ID NO 29
<211> LENGTH: 19
<212> TYPE: RNA
<213> ORGANISM: Artificial sequence
<220> FEATURE:
<223> OTHER INFORMATION: Synthetic siRNA sequence MUTYH

<400> SEQUENCE: 29
gguuguccac accuucucu                                                19

<210> SEQ ID NO 30
<211> LENGTH: 19
<212> TYPE: RNA
<213> ORGANISM: Artificial sequence
<220> FEATURE:
<223> OTHER INFORMATION: Synthetic siRNA sequence MUTYH

<400> SEQUENCE: 30
gcugacauau caaguauau                                                19

<210> SEQ ID NO 31
<211> LENGTH: 19
<212> TYPE: RNA
<213> ORGANISM: Artificial sequence
<220> FEATURE:
<223> OTHER INFORMATION: Synthetic siRNA sequence PNKP

<400> SEQUENCE: 31
cacacuguau uuggucaau                                                19

<210> SEQ ID NO 32
<211> LENGTH: 19
<212> TYPE: RNA
<213> ORGANISM: Artificial sequence
<220> FEATURE:
<223> OTHER INFORMATION: Synthetic siRNA sequence PNKP

<400> SEQUENCE: 32
agagacccgc acaccagaa                                                19

<210> SEQ ID NO 33
<211> LENGTH: 19
<212> TYPE: RNA
<213> ORGANISM: Artificial sequence
<220> FEATURE:
<223> OTHER INFORMATION: Synthetic siRNA sequence PNKP

<400> SEQUENCE: 33
gaaucuugua cccagagau                                                19
```

```
<210> SEQ ID NO 34
<211> LENGTH: 19
<212> TYPE: RNA
<213> ORGANISM: Artificial sequence
<220> FEATURE:
<223> OTHER INFORMATION: Synthetic siRNA sequence PNKP

<400> SEQUENCE: 34
aguccaccuu ucucaagaa                                                    19

<210> SEQ ID NO 35
<211> LENGTH: 19
<212> TYPE: RNA
<213> ORGANISM: Artificial sequence
<220> FEATURE:
<223> OTHER INFORMATION: Synthetic siRNA sequence PNKP

<400> SEQUENCE: 35
caaccgguuu cgagagaug                                                    19

<210> SEQ ID NO 36
<211> LENGTH: 19
<212> TYPE: RNA
<213> ORGANISM: Artificial sequence
<220> FEATURE:
<223> OTHER INFORMATION: Synthetic siRNA sequence POLD1

<400> SEQUENCE: 36
ggagauggag gcagaacac                                                    19

<210> SEQ ID NO 37
<211> LENGTH: 19
<212> TYPE: RNA
<213> ORGANISM: Artificial sequence
<220> FEATURE:
<223> OTHER INFORMATION: Synthetic siRNA sequence POLD1

<400> SEQUENCE: 37
guuggagauu gaccauuau                                                    19

<210> SEQ ID NO 38
<211> LENGTH: 19
<212> TYPE: RNA
<213> ORGANISM: Artificial Sequence
<220> FEATURE:
<223> OTHER INFORMATION: Synthetic siRNA sequence POLD1

<400> SEQUENCE: 38
ucaccgguua caacaucca                                                    19

<210> SEQ ID NO 39
<211> LENGTH: 19
<212> TYPE: RNA
<213> ORGANISM: Artificial sequence
<220> FEATURE:
<223> OTHER INFORMATION: Synthetic siRNA sequence POLD1

<400> SEQUENCE: 39
cuuagacucc accagcugc                                                    19

<210> SEQ ID NO 40
<211> LENGTH: 19
<212> TYPE: RNA
<213> ORGANISM: Artificial sequence
<220> FEATURE:
<223> OTHER INFORMATION: Synthetic siRNA sequence POLD1
```

```
<400> SEQUENCE: 40
auucagaugg gauaccucc                                                   19

<210> SEQ ID NO 41
<211> LENGTH: 19
<212> TYPE: RNA
<213> ORGANISM: Artificial sequence
<220> FEATURE:
<223> OTHER INFORMATION: Synthetic siRNA sequence RAD54L

<400> SEQUENCE: 41
ccagcauugu gaauagaug                                                   19

<210> SEQ ID NO 42
<211> LENGTH: 19
<212> TYPE: RNA
<213> ORGANISM: Artificial sequence
<220> FEATURE:
<223> OTHER INFORMATION: Synthetic siRNA sequence RAD54L

<400> SEQUENCE: 42
ucaccucgcu aaagaagcu                                                   19

<210> SEQ ID NO 43
<211> LENGTH: 19
<212> TYPE: RNA
<213> ORGANISM: Artificial sequence
<220> FEATURE:
<223> OTHER INFORMATION: Synthetic siRNA sequence RAD54L

<400> SEQUENCE: 43
ggagcuguuu auccuggau                                                   19

<210> SEQ ID NO 44
<211> LENGTH: 19
<212> TYPE: RNA
<213> ORGANISM: Artificial sequence
<220> FEATURE:
<223> OTHER INFORMATION: Synthetic siRNA sequence RAD54L

<400> SEQUENCE: 44
ugaucugcuu gaguauuuc                                                   19

<210> SEQ ID NO 45
<211> LENGTH: 19
<212> TYPE: RNA
<213> ORGANISM: Artificial sequence
<220> FEATURE:
<223> OTHER INFORMATION: Synthetic siRNA sequence RAD54L

<400> SEQUENCE: 45
gcagugagac ccagaucca                                                   19

<210> SEQ ID NO 46
<211> LENGTH: 19
<212> TYPE: RNA
<213> ORGANISM: Artificial sequence
<220> FEATURE:
<223> OTHER INFORMATION: Synthetic siRNA sequence RUVBL2

<400> SEQUENCE: 46
aucuucuccc uggagauga                                                   19

<210> SEQ ID NO 47
<211> LENGTH: 19
<212> TYPE: RNA
```

```
<213> ORGANISM: Artificial sequence
<220> FEATURE:
<223> OTHER INFORMATION: Synthetic siRNA sequence RUVBL2

<400> SEQUENCE: 47
acugacccuc aagaccaca                                                      19

<210> SEQ ID NO 48
<211> LENGTH: 19
<212> TYPE: RNA
<213> ORGANISM: Artificial sequence
<220> FEATURE:
<223> OTHER INFORMATION: Synthetic siRNA sequence RUVBL2

<400> SEQUENCE: 48
acgcaagggu acagaagug                                                      19

<210> SEQ ID NO 49
<211> LENGTH: 21
<212> TYPE: RNA
<213> ORGANISM: Artificial sequence
<220> FEATURE:
<223> OTHER INFORMATION: Synthetic siRNA sequence GFP

<400> SEQUENCE: 49
gacguaaacg gccacaaguu c                                                   21

<210> SEQ ID NO 50
<211> LENGTH: 19
<212> TYPE: RNA
<213> ORGANISM: Artificial sequence
<220> FEATURE:
<223> OTHER INFORMATION: Synthetic ERCC1

<400> SEQUENCE: 50
ggagcuggcu aagaugugu                                                      19

<210> SEQ ID NO 51
<211> LENGTH: 19
<212> TYPE: RNA
<213> ORGANISM: Artificial sequence
<220> FEATURE:
<223> OTHER INFORMATION: Synthetic siRNA sequence CYP2B6

<400> SEQUENCE: 51
ccaccauccu ccagaacuu                                                      19

<210> SEQ ID NO 52
<211> LENGTH: 19
<212> TYPE: RNA
<213> ORGANISM: Artificial sequence
<220> FEATURE:
<223> OTHER INFORMATION: Synthetic siRNA sequence CYP2B6

<400> SEQUENCE: 52
ggaaaucaau gcuuacauu                                                      19

<210> SEQ ID NO 53
<211> LENGTH: 19
<212> TYPE: RNA
<213> ORGANISM: Artificial sequence
<220> FEATURE:
<223> OTHER INFORMATION: Synthetic siRNA sequence CYP2B6

<400> SEQUENCE: 53
acaggugauu ggcccacau                                                      19
```

```
<210> SEQ ID NO 54
<211> LENGTH: 19
<212> TYPE: RNA
<213> ORGANISM: Artificial sequence
<220> FEATURE:
<223> OTHER INFORMATION: Synthetic siRNA sequence CYP2B6

<400> SEQUENCE: 54
ugacccacac uacuugaa                                                    19

<210> SEQ ID NO 55
<211> LENGTH: 19
<212> TYPE: RNA
<213> ORGANISM: Artificial sequence
<220> FEATURE:
<223> OTHER INFORMATION: Synthetic siRNA sequence CYP2B6

<400> SEQUENCE: 55
acacgcucuc gcucuucuu                                                   19

<210> SEQ ID NO 56
<211> LENGTH: 19
<212> TYPE: RNA
<213> ORGANISM: Artificial sequence
<220> FEATURE:
<223> OTHER INFORMATION: Synthetic siRNA sequence CYP2F1

<400> SEQUENCE: 56
ccacacauaa ccugcucuu                                                   19

<210> SEQ ID NO 57
<211> LENGTH: 19
<212> TYPE: RNA
<213> ORGANISM: Artificial sequence
<220> FEATURE:
<223> OTHER INFORMATION: Synthetic siRNA sequence CYP2F1

<400> SEQUENCE: 57
gcauaagcac agccaucuu                                                   19

<210> SEQ ID NO 58
<211> LENGTH: 19
<212> TYPE: RNA
<213> ORGANISM: Artificial sequence
<220> FEATURE:
<223> OTHER INFORMATION: Synthetic siRNA sequence CYP2F1

<400> SEQUENCE: 58
ucaaugacaa cuuccaaau                                                   19

<210> SEQ ID NO 59
<211> LENGTH: 19
<212> TYPE: RNA
<213> ORGANISM: Artificial sequence
<220> FEATURE:
<223> OTHER INFORMATION: Synthetic siRNA sequence CYP2F1

<400> SEQUENCE: 59
acacggaguu cuacuugaa                                                   19

<210> SEQ ID NO 60
<211> LENGTH: 19
<212> TYPE: RNA
<213> ORGANISM: Artificial sequence
<220> FEATURE:
<223> OTHER INFORMATION: Synthetic siRNA sequence CYP2F1
```

```
<400> SEQUENCE: 60
ccaccgucau gcagaacuu                                          19

<210> SEQ ID NO 61
<211> LENGTH: 19
<212> TYPE: RNA
<213> ORGANISM: Artificial sequence
<220> FEATURE:
<223> OTHER INFORMATION: Synthetic siRNA sequence CYP2A6

<400> SEQUENCE: 61
ugaccacguu gaaccucuu                                          19

<210> SEQ ID NO 62
<211> LENGTH: 19
<212> TYPE: RNA
<213> ORGANISM: Artificial sequence
<220> FEATURE:
<223> OTHER INFORMATION: Synthetic siRNA sequence CYP2A6

<400> SEQUENCE: 62
ccaaguuucg ggauuucuu                                          19

<210> SEQ ID NO 63
<211> LENGTH: 19
<212> TYPE: RNA
<213> ORGANISM: Artificial sequence
<220> FEATURE:
<223> OTHER INFORMATION: Synthetic siRNA sequence CYP2A6

<400> SEQUENCE: 63
gcaccagcau cguuguaga                                          19

<210> SEQ ID NO 64
<211> LENGTH: 19
<212> TYPE: RNA
<213> ORGANISM: Artificial sequence
<220> FEATURE:
<223> OTHER INFORMATION: Synthetic siRNA sequence CYP2A6

<400> SEQUENCE: 64
ggacaaagag uuccuguca                                          19

<210> SEQ ID NO 65
<211> LENGTH: 19
<212> TYPE: RNA
<213> ORGANISM: Artificial sequence
<220> FEATURE:
<223> OTHER INFORMATION: Synthetic siRNA sequence CYP2A6

<400> SEQUENCE: 65
gcaagccugu caccuuugu                                          19

<210> SEQ ID NO 66
<211> LENGTH: 19
<212> TYPE: RNA
<213> ORGANISM: Artificial sequence
<220> FEATURE:
<223> OTHER INFORMATION: Synthetic siRNA sequence CYPAB1

<400> SEQUENCE: 66
ugagccugac uaugccaaa                                          19

<210> SEQ ID NO 67
<211> LENGTH: 19
<212> TYPE: RNA
```

```
<213> ORGANISM: Artificial sequence
<220> FEATURE:
<223> OTHER INFORMATION: Synthetic siRNA sequence CYPAB1

<400> SEQUENCE: 67
ugaugugcug aagcccuau                                                19

<210> SEQ ID NO 68
<211> LENGTH: 19
<212> TYPE: RNA
<213> ORGANISM: Artificial sequence
<220> FEATURE:
<223> OTHER INFORMATION: Synthetic siRNA sequence CYPAB1

<400> SEQUENCE: 68
ggagucuacu cgcuucuau                                                19

<210> SEQ ID NO 69
<211> LENGTH: 19
<212> TYPE: RNA
<213> ORGANISM: Artificial sequence
<220> FEATURE:
<223> OTHER INFORMATION: Synthetic siRNA sequence CYPAB1

<400> SEQUENCE: 69
gcacgaucau ucuucucau                                                19

<210> SEQ ID NO 70
<211> LENGTH: 19
<212> TYPE: RNA
<213> ORGANISM: Artificial sequence
<220> FEATURE:
<223> OTHER INFORMATION: Synthetic siRNA sequence CYPAB1

<400> SEQUENCE: 70
cuaccuugca gucagcgau                                                19

<210> SEQ ID NO 71
<211> LENGTH: 19
<212> TYPE: RNA
<213> ORGANISM: Artificial sequence
<220> FEATURE:
<223> OTHER INFORMATION: Synthetic siRNA sequence FRAP1

<400> SEQUENCE: 71
agaacucgcu gauccaaau                                                19

<210> SEQ ID NO 72
<211> LENGTH: 19
<212> TYPE: RNA
<213> ORGANISM: Artificial sequence
<220> FEATURE:
<223> OTHER INFORMATION: Synthetic siRNA sequence FRAP1

<400> SEQUENCE: 72
ccagcagcau aagcaggaa                                                19

<210> SEQ ID NO 73
<211> LENGTH: 19
<212> TYPE: RNA
<213> ORGANISM: Artificial sequence
<220> FEATURE:
<223> OTHER INFORMATION: Synthetic siRNA sequence FRAP1

<400> SEQUENCE: 73
caagcgacau cccaugaaa                                                19
```

<210> SEQ ID NO 74
<211> LENGTH: 19
<212> TYPE: RNA
<213> ORGANISM: Artificial sequence
<220> FEATURE:
<223> OTHER INFORMATION: Synthetic siRNA sequence FRAP1

<400> SEQUENCE: 74
gcaggcugcu cuccauggu                                              19

<210> SEQ ID NO 75
<211> LENGTH: 19
<212> TYPE: RNA
<213> ORGANISM: Artificial sequence
<220> FEATURE:
<223> OTHER INFORMATION: Synthetic siRNA sequence FRAP1

<400> SEQUENCE: 75
ggcucaugcu gggacccaa                                              19

<210> SEQ ID NO 76
<211> LENGTH: 19
<212> TYPE: RNA
<213> ORGANISM: Artificial sequence
<220> FEATURE:
<223> OTHER INFORMATION: Synthetic siRNA sequence MGC13170

<400> SEQUENCE: 76
ggagcugucc auacgccac                                              19

<210> SEQ ID NO 77
<211> LENGTH: 19
<212> TYPE: RNA
<213> ORGANISM: Artificial sequence
<220> FEATURE:
<223> OTHER INFORMATION: Synthetic siRNA sequence MGC13170

<400> SEQUENCE: 77
ggagaaggug gauaagugg                                              19

<210> SEQ ID NO 78
<211> LENGTH: 19
<212> TYPE: RNA
<213> ORGANISM: Artificial sequence
<220> FEATURE:
<223> OTHER INFORMATION: Synthetic siRNA sequence MGC13170

<400> SEQUENCE: 78
ccaggcucau gcugggacc                                              19

<210> SEQ ID NO 79
<211> LENGTH: 19
<212> TYPE: RNA
<213> ORGANISM: Artificial sequence
<220> FEATURE:
<223> OTHER INFORMATION: Synthetic siRNA sequence MLP

<400> SEQUENCE: 79
cgagggcacu gcucaggaa                                              19

<210> SEQ ID NO 80
<211> LENGTH: 19
<212> TYPE: RNA
<213> ORGANISM: Artificial sequence
<220> FEATURE:
<223> OTHER INFORMATION: Synthetic siRNA sequence MLP -continued

```
<400> SEQUENCE: 80
gaagaaauuc ucuuucaag                                           19

<210> SEQ ID NO 81
<211> LENGTH: 19
<212> TYPE: RNA
<213> ORGANISM: Artificial sequence
<220> FEATURE:
<223> OTHER INFORMATION: Synthetic siRNA sequence MLP

<400> SEQUENCE: 81
aaagcaaugg agacuuauc                                           19

<210> SEQ ID NO 82
<211> LENGTH: 19
<212> TYPE: RNA
<213> ORGANISM: Artificial sequence
<220> FEATURE:
<223> OTHER INFORMATION: Synthetic siRNA sequence MLP

<400> SEQUENCE: 82
cgacuucguu cuaauauau                                           19

<210> SEQ ID NO 83
<211> LENGTH: 19
<212> TYPE: RNA
<213> ORGANISM: Artificial sequence
<220> FEATURE:
<223> OTHER INFORMATION: Synthetic siRNA sequence MLP

<400> SEQUENCE: 83
ucaacuuccu ucagaauuu                                           19

<210> SEQ ID NO 84
<211> LENGTH: 19
<212> TYPE: RNA
<213> ORGANISM: Artificial sequence
<220> FEATURE:
<223> OTHER INFORMATION: Synthetic siRNA sequence MSH4

<400> SEQUENCE: 84
guagacgacu ucguucuaa                                           19

<210> SEQ ID NO 85
<211> LENGTH: 19
<212> TYPE: RNA
<213> ORGANISM: Artificial sequence
<220> FEATURE:
<223> OTHER INFORMATION: Synthetic siRNA sequence MSH4

<400> SEQUENCE: 85
agagcuuacu augguuccu                                           19

<210> SEQ ID NO 86
<211> LENGTH: 19
<212> TYPE: RNA
<213> ORGANISM: Artificial sequence
<220> FEATURE:
<223> OTHER INFORMATION: Synthetic siRNA sequence MSH4

<400> SEQUENCE: 86
agaagguauu ggcauuugu                                           19

<210> SEQ ID NO 87
<211> LENGTH: 19
<212> TYPE: RNA
```

```
<213> ORGANISM: Artificial sequence
<220> FEATURE:
<223> OTHER INFORMATION: Synthetic siRNA sequence MSH4

<400> SEQUENCE: 87
gcugacuccu gaggaagaa                                                      19

<210> SEQ ID NO 88
<211> LENGTH: 19
<212> TYPE: RNA
<213> ORGANISM: Artificial sequence
<220> FEATURE:
<223> OTHER INFORMATION: Synthetic siRNA sequence RPS8

<400> SEQUENCE: 88
ccacaagaag cggaaguau                                                      19

<210> SEQ ID NO 89
<211> LENGTH: 19
<212> TYPE: RNA
<213> ORGANISM: Artificial sequence
<220> FEATURE:
<223> OTHER INFORMATION: Synthetic siRNA sequence RPS8

<400> SEQUENCE: 89
agaguuggag uucuaucuu                                                      19

<210> SEQ ID NO 90
<211> LENGTH: 19
<212> TYPE: RNA
<213> ORGANISM: Artificial sequence
<220> FEATURE:
<223> OTHER INFORMATION: Synthetic siRNA sequence RPS8

<400> SEQUENCE: 90
agagaaagcc cuaccacaa                                                      19

<210> SEQ ID NO 91
<211> LENGTH: 19
<212> TYPE: RNA
<213> ORGANISM: Artificial sequence
<220> FEATURE:
<223> OTHER INFORMATION: Synthetic siRNA sequence CYP2B6

<400> SEQUENCE: 91
ccagggagag gaguuuagu                                                      19

<210> SEQ ID NO 92
<211> LENGTH: 19
<212> TYPE: RNA
<213> ORGANISM: Artificial sequence
<220> FEATURE:
<223> OTHER INFORMATION: Synthetic siRNA sequence CYP2B6

<400> SEQUENCE: 92
gaagcauuga ggagcgaau                                                      19

<210> SEQ ID NO 93
<211> LENGTH: 19
<212> TYPE: RNA
<213> ORGANISM: Artificial sequence
<220> FEATURE:
<223> OTHER INFORMATION: Synthetic siRNA sequence ERCC2

<400> SEQUENCE: 93 gcauuccca ucgacgucc                                                       19
```

```
<210> SEQ ID NO 94
<211> LENGTH: 19
<212> TYPE: RNA
<213> ORGANISM: Artificial sequence
<220> FEATURE:
<223> OTHER INFORMATION: Synthetic siRNA sequence ERCC2

<400> SEQUENCE: 94
ucaaagggcu cgaugauga                                               19

<210> SEQ ID NO 95
<211> LENGTH: 19
<212> TYPE: RNA
<213> ORGANISM: Artificial sequence
<220> FEATURE:
<223> OTHER INFORMATION: Synthetic siRNA sequence ERCC2

<400> SEQUENCE: 95
auaaagagca gcuuguucc                                               19

<210> SEQ ID NO 96
<211> LENGTH: 19
<212> TYPE: RNA
<213> ORGANISM: Artificial sequence
<220> FEATURE:
<223> OTHER INFORMATION: Synthetic siRNA sequence ERCC2

<400> SEQUENCE: 96
aucgaaggua agaaaguca                                               19

<210> SEQ ID NO 97
<211> LENGTH: 19
<212> TYPE: RNA
<213> ORGANISM: Artificial sequence
<220> FEATURE:
<223> OTHER INFORMATION: Synthetic siRNA sequence MUTYH

<400> SEQUENCE: 97
auauacuuga uaugucagc                                               19

<210> SEQ ID NO 98
<211> LENGTH: 19
<212> TYPE: RNA
<213> ORGANISM: Artificial sequence
<220> FEATURE:
<223> OTHER INFORMATION: Synthetic siRNA sequence PNPK

<400> SEQUENCE: 98
auugaccaaa uacagugug                                               19

<210> SEQ ID NO 99
<211> LENGTH: 19
<212> TYPE: RNA
<213> ORGANISM: Artificial sequence
<220> FEATURE:
<223> OTHER INFORMATION: Synthetic siRNA sequence POLD1

<400> SEQUENCE: 99
uggauguugu aaccgguga                                               19

<210> SEQ ID NO 100
<211> LENGTH: 19
<212> TYPE: RNA
<213> ORGANISM: Artificial sequence
<220> FEATURE:
<223> OTHER INFORMATION: Synthetic siRNA sequence RUVBL2
```

```
<400> SEQUENCE: 100
ucaucuccag ggagaagau                                                    19

<210> SEQ ID NO 101
<211> LENGTH: 19
<212> TYPE: RNA
<213> ORGANISM: Artificial sequence
<220> FEATURE:
<223> OTHER INFORMATION: Synthetic siRNA sequence CYP2A

<400> SEQUENCE: 101
ugacaggaac ucuuugucc                                                    19

<210> SEQ ID NO 102
<211> LENGTH: 19
<212> TYPE: RNA
<213> ORGANISM: Artificial sequence
<220> FEATURE:
<223> OTHER INFORMATION: Synthetic siRNA sequence CYP4B1

<400> SEQUENCE: 102
aucgcugacu gcaagguag                                                    19

<210> SEQ ID NO 103
<211> LENGTH: 19
<212> TYPE: RNA
<213> ORGANISM: Artificial sequence
<220> FEATURE:
<223> OTHER INFORMATION: Synthetic siRNA sequence MGC13170

<400> SEQUENCE: 103
gugcagccuc agaagaaga                                                    19

<210> SEQ ID NO 104
<211> LENGTH: 19
<212> TYPE: RNA
<213> ORGANISM: Artificial sequence
<220> FEATURE:
<223> OTHER INFORMATION: Synthetic siRNA sequence MGC13170

<400> SEQUENCE: 104
gaagaagaaa uucucuuuc                                                    19

<210> SEQ ID NO 105
<211> LENGTH: 19
<212> TYPE: RNA
<213> ORGANISM: Artificial sequence
<220> FEATURE:
<223> OTHER INFORMATION: Synthetic siRNA sequence MSH4

<400> SEQUENCE: 105
ccaagacccu ggugaagaa                                                    19
```